(12) United States Patent
Gupta et al.

(10) Patent No.: US 9,486,005 B2
(45) Date of Patent: Nov. 8, 2016

(54) AGENTS AND MECHANISMS FOR TREATING HYPERCHOLESTEROLEMIA

(76) Inventors: Smiti Vaid Gupta, Oakland Township, MI (US); Enrique Martinez, II, Clinton Township, MI (US); Fazlul H. Sarkar, Plymouth, MI (US); Denis M. Callewaert, Metamora, MI (US); Andreea Geamanu, Sterling Heights, MI (US); Kevin Michael Patrie, Troy, MI (US); Tiffany Capri Thomas, Scottsdale, AZ (US); Andrew A. Dahl, Bloomfield Hills, MI (US)

(*) Notice: Subject to any disclaimer, the term of this patent is extended or adjusted under 35 U.S.C. 154(b) by 0 days.

(21) Appl. No.: 13/580,471

(22) PCT Filed: Feb. 22, 2011

(86) PCT No.: PCT/US2011/025713
§ 371 (c)(1),
(2), (4) Date: Aug. 22, 2012

(87) PCT Pub. No.: WO2011/103569
PCT Pub. Date: Aug. 25, 2011

(65) Prior Publication Data
US 2012/0328598 A1 Dec. 27, 2012

Related U.S. Application Data

(60) Provisional application No. 61/306,591, filed on Feb. 22, 2010, provisional application No. 61/311,838, filed on Mar. 9, 2010.

(51) Int. Cl.
*A61K 36/02* (2006.01)
*A23L 1/30* (2006.01)
*A23L 1/305* (2006.01)

(52) U.S. Cl.
CPC .................. *A23L 1/30* (2013.01); *A23L 1/305* (2013.01); *A23V 2002/00* (2013.01)

(58) Field of Classification Search
CPC ....................................................... A23L 1/30
See application file for complete search history.

(56) References Cited

U.S. PATENT DOCUMENTS

2008/0119571 A1* 5/2008 Khanna et al. ............... 514/789
2013/0251698 A1* 9/2013 Thomas ................. A61K 38/16
424/94.1

OTHER PUBLICATIONS

Oben et al., The effects of ProAlgaZyme novel algae infusion on metabolic syndrome and markers of cardiovascular health, 2007, Lipids Health Dis. 6: 20.*
Oben et al., The effects of ProAlgaZyme novel algae infusion on metabolic syndrome and markers of cardiovascular health, 2007, Lipids Health Dis 6: 20.*
"Analogue." Merriam-Webster.com. Merriam-Webster, n.d. Web. Aug. 21, 2014. <http://www.merriam-webster.com/dictionary/analogue>.*

* cited by examiner

*Primary Examiner* — Robert Yamasaki
(74) *Attorney, Agent, or Firm* — Kenneth I. Kohn

(57) ABSTRACT

A method of treating hypercholesterolemia in mammals, by administering an effective amount of a microbial fermentation product, and regulating genes involved in lipoprotein metabolism. A method of regulating cholesterol levels in a patient by administering an effective amount of a composition chosen from the group consisting of PAZ, specific components isolated from PAZ, chemically synthesized analogs of the components of PAZ, and regulating genes involved in lipoprotein metabolism. A method of treating high cholesterol levels in an individual by administering an effective amount of a microbial fermentation product, up-regulating the expression of at least one of the genes that encode ABCA1, ApoA1, and SRB1, and down-regulating the gene that encodes CETP. A method of preventing the onset of high cholesterol levels and/or a deleterious lipoprotein profile in an individual.

3 Claims, 33 Drawing Sheets

VLDL, d = 0.94-1.006 g/ml), intermediate density lipoproteins (IDL, d = 1.006-1.019 g/ml), low density lipoproteins (LDL, d = 1.019-1.063 g/ml), high density lipoproteins (HDL, d = 1.063-1.210 g/ml)

Shift in Lipoprotein composition from lower to higher density particles in water vs F3 fed hamsters Effect of PAZ on the expression of mRNA encoding CETP by cultured HEPG2 cells determined by real time qPCR

|        | T2/PE4 lot 3 | PE4 lot 1/30 | PE4n lot#30 | PW1    | PW2    |
|--------|--------------|--------------|-------------|--------|--------|
| TC     | 234.69       | 229.00       | 214.00      | 237.00 | 224.00 |
| HDL    | 143.17       | 138.00       | 108.00      | 105.00 | 108.00 |
| TC/HDL | 1.63         | 1.67         | 2.28        | 2.27   | 2.44   |
| non HDL| 86.54        | 91.20        | 139.00      | 132.00 | 140.00 |
| TG     | 222.10       | 171.00       | 158.00      | 202.00 | 152.00 |

FIGURE 33

AGENTS AND MECHANISMS FOR TREATING HYPERCHOLESTEROLEMIA

BACKGROUND OF THE INVENTION

1. Technical Field

The present invention relates to extractions from algae. In particular, the present invention relates to cholesterol-lowering extractions from algae and extractions that have the ability to favorably shift the HDL/LDL profile in mammals.

2. Background Art

Cholesterol is a waxy, fat-like substance made in the liver and found in certain foods, such as food from animals, like dairy products, eggs, and meat. The body needs some cholesterol in order to function properly: cell membranes, need cholesterol in order to produce hormones, such as estrogen and vitamin D, and the bile acids that help to digest fat and excrete certain waste products. However, when too much cholesterol is present, whether due to excessive dietary intake, excessive production or a decreased ability to eliminate excessive quantities, health problems such as heart disease can develop.

When too much cholesterol is present, plaque (a thick, hard deposit) can form in the body's arteries narrowing the space for blood to flow to the heart, brain and other tissues. Over time, this buildup causes atherosclerosis (hardening of the arteries), which can lead to cardiovascular diseases. When not enough oxygen-carrying blood reaches the heart, chest pain, e.g. angina, can result. If the blood supply to a portion of the heart is completely cut off by total blockage of a coronary artery, these results in the damage and death or heart cells, an event commonly called a heart attack. This is usually due to a sudden closure from a blood clot forming on top of a previous narrowing.

Lipoprotein metabolism has a key role in atherogenesis, which is the buildup of atherosclerotic plaque. Lipoprotein metabolism is a complex and interconnected group of processes that involve the receptors for lipoproteins, a family of core proteins (called apolipoproteins) around which lipids assemble to form lipoproteins, as well as the transport of lipids, particularly cholesterol and triglycerides, and their exchange between different lipoprotein classes in the blood. The intestine absorbs dietary fat and packages it into chylomicrons (large triglyceride-rich lipoproteins), which are transported to peripheral tissues through the blood. In muscle and adipose tissues, the enzyme lipoprotein lipase breaks down chylomicrons, and fatty acids enter these tissues. The chylomicron remnants are subsequently taken up by the liver. The liver loads lipids onto ApoB and secretes very-low-density lipoproteins (VLDLs), which undergo lipolysis by lipoprotein lipase to form low-density lipoproteins (LDLs). LDLs are then taken up by the liver through binding to the LDL receptor (LDLR), as well as through other pathways. By contrast, high-density lipoproteins (HDLs) are generated by the intestine and the liver through the secretion of lipid-free ApoA1. ApoA1 then recruits cholesterol from these organs through the actions of the transporter ABCA1, forming nascent HDLs, and this protects ApoA1 from being rapidly degraded in the kidneys. In the peripheral tissues, nascent HDLs promote the efflux of cholesterol from tissues, including from macrophages, through the actions of ABCA1. Mature HDLs also promote this efflux but through the actions of ABCG1. (In macrophages, the nuclear receptor LXR up-regulates the production of both ABCA1 and ABCG1, this seems out of context here) The free (unesterified) cholesterol in nascent HDLs is esterified to cholesteryl esters by the enzyme lecithin cholesterol acyltransferase (LCAT), creating mature HDLs. The cholesterol in HDLs is returned to the liver both directly, through uptake by the receptor SR-BI, and indirectly, by transfer to LDLs and VLDLs through the cholesteryl ester transfer protein (CETP). The lipid content of HDLs is altered by the enzymes hepatic lipase and endothelial lipase and by the transfer proteins CETP and phospholipid transfer protein (PLTP), affecting HDL catabolism.

LDLs can cause buildup of plaque on the walls of arteries, and their presence in large amounts indicates a risk for heart disease. HDLs in contrast, aid the body in eliminating LDLs and thus reduce heart disease. A low level of HDL also puts your body at risk for cardiovascular diseases, as the natural mechanism of eliminating LDL is reduced. Various factors can affect the amount of LDLs and HDLs that are present, such as diet, weight, exercise, age, gender, diabetes, heredity, and other medical conditions.

Statins are most commonly used to treat individuals with high cholesterol. Statins are inhibitors of the enzyme hydroxymethylglutaryl-coenzymeA reductase (HMG-CoA Reductase). Through inhibition of HMGCo Reductase, statins decrease cholesterol synthesis, and activate sterol regulatory element binding proteins (SREBPs). SREBP bind with sterol response elements (SREs). This up-regulates LDL-R gene transcription, providing an increased expression of LDL-receptors in the hepatocellular membrane and an increased cellular uptake of LDL molecules. There are several side effects reported with statin use, including myopathy, rhabdomyolysis—increased inflammation, muscle breakdown, and renal overload. Some statins, e.g. lipitor and crestor, appear to also exhibit the additional beneficial effect of inhibiting the function of CETP.

Several other treatments have been developed to combat high cholesterol, especially in food supplements. Omega-3 fatty acids are effective but lack abundant environmentally-sustainable sources. Resveratrol is a very popular treatment and is produced naturally by plants. Acai berry is also used; however, side effects are now showing up. Lingonberry and other extracts are being tested in clinical studies. Curcumin and isoflavonids are also gaining popularity. The priority of each of these supplements is to improve cardiovascular risk factors, cholesterol regulation, mental function, and weight loss.

There remains a need for a treatment for safely and effectively reducing circulating cholesterol levels and managing the HDL/LDL ratio without the incurrence of side effects. There is a further need of alternatives to current statin therapy that either have fewer deleterious side effects and/or function by a different mechanism, such as regulating cholesterol and/or lipoprotein metabolism at the genetic level.

SUMMARY OF THE INVENTION

The present invention provides for a method of treating hypercholesterolemia in a patient, by administering an effective amount of a microbial fermentation product, and regulating genes involved in lipoprotein metabolism.

The present invention provides for a method of regulating cholesterol levels in a patient by administering an effective amount of a composition chosen from the group consisting of PAZ, specific components isolated from PAZ, chemically synthesized analogues of the components of PAZ, and regulating genes involved in lipoprotein metabolism.

The present invention also provides for a method of treating high cholesterol levels in a patient by administering an effective amount of a microbial fermentation product, up-regulating the expression of at least one of the genes that encode ABCA1, ApoA1, and SR-B1, and down-regulating the gene that encodes CETP.

The present invention further provides for a method of preventing the onset of high cholesterol by administering an effective amount of a composition chosen from the group consisting of PAZ, specific components isolated from PAZ, chemically synthesized analogues of the components of PAZ, regulating genes involved in lipoprotein metabolism, and preventing the onset of high cholesterol.

DESCRIPTION OF THE DRAWINGS

Other advantages of the present invention are readily appreciated as the same becomes better understood by reference to the following detailed description when considered in connection with the accompanying drawings wherein:

FIG. 33 is a table summarizing the results of different studies of the effects of PAZ fraction PF4 on various plasma lipid parameters. PF4 lot 1/30 and PF4n lot 3/30 represent the results obtained in a preventative experimental model in which hamsters were fed a high fat diet plus the PF4 fraction of different PAZ lots (the representative water control results are found in column PW1). T21/PF4 lot 3 represents results obtained from a therapeutic experimental model in which hamsters were fed a high-fat diet for 4 weeks to induce hypercholesterolemia, and then treated for an additional 21 days with the high fat diet plus either PAZ fraction PF4 or water (PW2) without any additives.

DETAILED DESCRIPTION OF THE INVENTION

Figure 1:
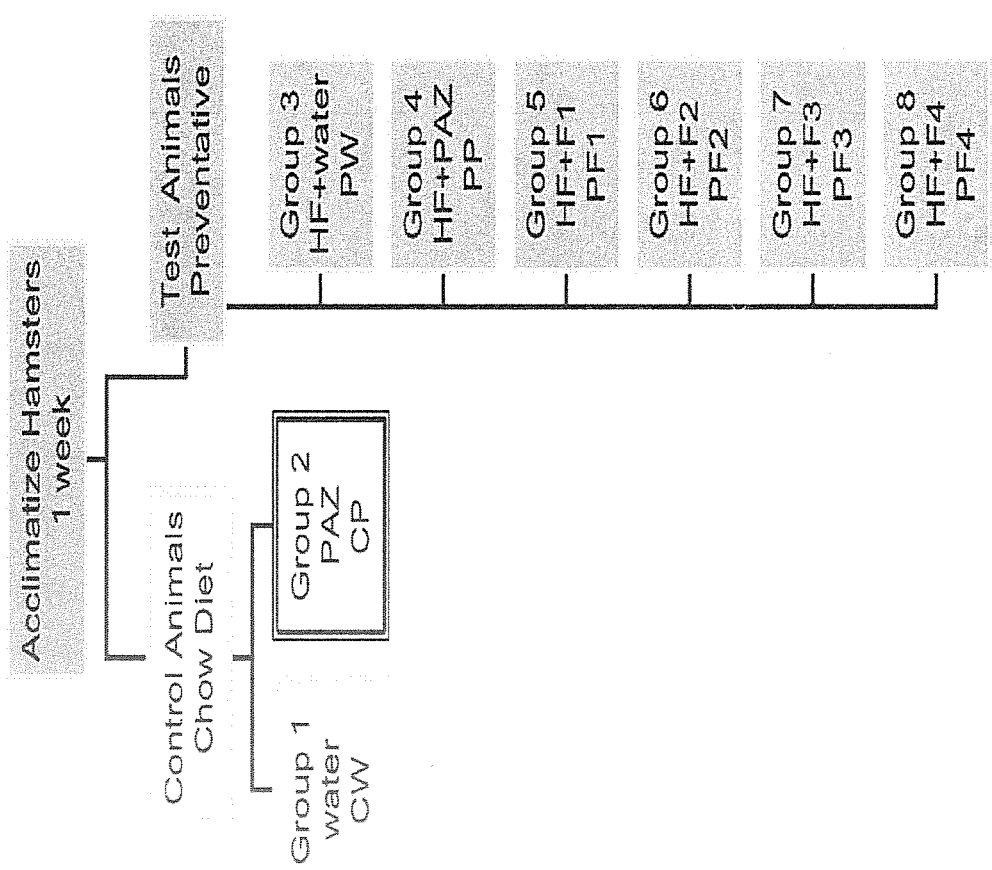
FIG. 1 is a flow chart outlining animal studies performed in an in vivo preventative experimental model in hamsters in which a high fat diet was used to produce elevated cholesterol levels and the effect of PAZ and fractions derived therefrom based on differential chemical properties were evaluated for their ability to alter cholesterol metabolism.

The present invention provides generally for a method of treating an individual (i.e. a human patient or animal) having high or abnormal cholesterol levels, i.e. hypercholesterolemia, through the use of a complex microbial fermentation product. More specifically, the present invention provides for mechanisms of action whereby certain components of the complex microbial fermentation product influence the cholesterol metabolism pathway and regulate genes involved in lipoprotein metabolism.

"ProAlgaZyme™" (also referred to as PAZ) is a novel fermentation product of a freshwater algae ecosystem that has been used as a dietary supplement for over 3 decades. PAZ was first marketed in the U.S. as Lebenszeit™, meaning "Lifetime" in German, in the 1980's by Ponce de Leon Medical Development Corp., in reference to the legendary fountain of youth. The product became what is known today as ProAlgaZyme® (PAZ) in 2003. The infusion is an aqueous fermentation product of a proprietary blend of freshwater organisms discovered over 30 years ago within a natural source, and has since been cultivated under controlled conditions. A deposit of a culture resulting in ProAlgaZyme aqueous extract or PAZ of the present invention has been placed in the American Type Culture Collection, of Manassas, Va., as Deposit #PTA-5863. ProAlgaZyme oral liquid dietary supplement, a consumable filtrate of the fermentation process, typically has less than 100 ppm total dissolved solids consisting of approximately 90% salts (free of heavy metals at a detection limit of <0.1 ppm) and a unique blend of organic constituents. PAZ has also previously been referred to as a phyto-percolate.

PAZ components can be isolated from the ProAlgaZyme algal fermentation medium described below or they can be produced by any appropriate method known in the art. Suitable methods for producing the PAZ and derivatives include, for example, recombinantly or naturally expressing the protein(s) using a microorganism, synthetically producing a derivative (i.e., chemical (cell-free) synthesis), or by extracting the derivative or active compounds from the culture media or cellular contents of one or more of the species present in ATCC Deposit #PTA-5863. When the PAZ and its derivatives are produced using a microorganism, any suitable naturally occurring or recombinant microorganism can be used. The PAZ and its derivatives are produced using naturally-occurring species present in ATCC Deposit #PTA-5863, or a recombinant variant thereof.

A method of making the inventive PAZ is also disclosed. The PAZ is prepared by first cultivating a mixture of aquatic organisms found within ATCC Deposit #PTA-5863 that is augmented by a specific nutrient blend forming a fortified algal and bacterial culture. Added to this fortified culture is purified fresh water that has been purified by reverse osmosis, distillation, deionization or other means. The culture is incubated with said purified fresh water and nutrient blend for a predetermined time forming an extract that is biologically active in nature. The extract is decanted from the fortified algal and bacterial culture and processed. Suitable methods of processing the extract include filtration, centrifugation, lyophilization, dialysis, purification, evaporation, concentration, dilution, formulation and other methods. The processing of the decanted extract in one particular method is by micro-filtration where the micro-filtration removes particles larger than about 0.22 μm.

In U.S. patent application Ser. No. 11/587,266, incorporated herein, PAZ source cultures are made of about 100-200 ml or about 0.1 to about 500 g or more fresh weight of dense algal, moss, fungal, and bacterial cells found within ATCC Deposit #PTA-5863 in about 2.5 gal (about 10 liters) of deionized filtered water. In this method, the cultures are grown under fluorescent or full-spectrum lights in an approximate 12:12 hour light/dark cycle at between about 15° C. and 37° C., particularly about 25° C. The cultures are grown in clear glass drum-shaped fishbowl-type containers having an approximate volume of 2.5 gal (about 10 liters) with semi-transparent lids that allow ambient gas exchange. Cultures are fed liquid extract of live active yeast, or Baker's yeast, Saccharomyces cerevisiae, which has been prepared from 1.0 g dry active yeast added to 50 ml warm sterile deionized water, at between about 37° C. and about 43° C. The yeast mixture is stirred and allowed to incubate at room temperature for about 10-30 minutes, or until it slightly foams. Each culture is fed approximately 1 ml of the prepared yeast mixture about one or more times between the times the culture is refilled and harvested, as defined below. It is contemplated within the scope of the invention that other yeast cultures and methods can be used. It is further contemplated that other culture conditions, materials and methods known in the art can be used if they support the production of PAZ, its components, active compounds and derivatives, including multi-species culture or monoculture, batch, semi-continuous, continuous or other culture systems, bioreactors, photoreactors or other fermentation technology, or through the use of other appropriate sources, substrates or carriers.

The culture fluid or PAZ can be harvested periodically by drawing off the top portion of fluid from each culture. This process is referred to as "harvest" and the resulting liquid is referred to as "PAZ", "ProAlgaZyme" or "aqueous extract" and can be subjected to further processing. Here, the majority of the algal cells forming the culture remain in the bottom of the culture container substantially undisturbed while PAZ is decanted from each culture. Various materials and methods known in the art can be used to harvest and batch the decanted PAZ after harvest, before or after filtration or further processing. After harvesting, PAZ is then filtered and consumed as desired. It has been found to have biological activity and be safe for consumption. The liquid volume of the growth container can then be returned to original volume using reverse-osmosis purified or deionized, filtered water at approximately room temperature (about 25° C.). It is contemplated that other methods or systems of harvest, extraction, processing, purification or compound isolation can be used for production of the PAZ and its derivatives if appropriate, including the absence of processing. It is further contemplated that PAZ can be bottled, concentrated, diluted, dried, or formulated with other ingredients, for example, or otherwise treated or employed.

Individual active compounds isolated from PAZ or their synthetic equivalents that are effective to lower a patient's cholesterol level can be used independently, or they may be combined to lower cholesterol as well as function to treat other diseases as described herein. Preferably, the treatment can be restricted to one or more substances isolated and characterized in PAZ, that is (are) chemically synthesized and is (are) administered in the absence or inactive components.

"Therapeutically effective amount", as used herein, refers to an amount of the composition of the present invention that will alleviate symptoms of a disease state or medical condition, preferably high LDL or total cholesterol levels and low HDL cholesterol levels. Further dosing regimens can be found in the examples below. Preferably, PAZ is administered as a liquid oral supplement, but the dosing of synthetic compounds that are identified to be responsible for the observed activities is likely to be in the form of capsules that are administered orally with concentration(s) in the range of mg or μg daily. For example, about 1 or more ounces per day in generally non-symptomatic subjects can be administered and about 3 or more ounces per day in diseased subjects can be administered. Further dosing regimens can be found in the examples below.

The present invention provides for a method of treating hypercholesterolemia in a patient, by administering an effective amount of a microbial fermentation product, and regulating genes involved in lipoprotein metabolism. By administering the microbial fermentation product, i.e. PAZ, its isolated components or chemically synthesized analogues thereof, one or more of the genes involved in lipoprotein metabolism and/or cholesterol can be either up- or down-regulated. This method is described in more detail below.

More specifically, the present invention provides for a method of regulating cholesterol levels in a patient by administering an effective amount of a composition chosen from the group consisting of PAZ, specific components isolated from PAZ, and chemically synthesized analogues of the components of PAZ, and regulating genes involved in lipoprotein metabolism. Preferably, the composition is in the form of a liquid oral supplement, however other forms described herein can also be used. The composition can also be in the form of a nutraceutical, and can further be a food additive. Preferably, administration of the composition is daily, however other administration profiles can be used as described herein.

Various genes are up-regulated and down-regulated by administering the composition. Transcription of the ApoA1 and SRB1 genes is up-regulated, whereas transcription of the gene encoding CETP is down-regulated. Therefore, more generally, high LDL and total cholesterol (TC) and low HDL cholesterol can be treated by up-regulating at least one of the genes encoding ABCA1, ApoA1, and SRB1, and/or down-regulating the gene that encodes CETP. More specifically, TC levels can be lowered, LDL levels can be lowered and HDL levels can be raised by administering PAZ. The up-regulation and down-regulation of these genes can be confirmed by performing an assay, such as by taking a plasma or blood sample from the patient and analyzing for TC, HDL, and LDL, or by using a commonly available method.

The present invention also provides for a method of treating high cholesterol levels in a patient by administering an effective amount of the microbial fermentation product, up-regulating the expression of at least one of the genes that encode ABCA1, ApoA1, and SRB1, and/or down-regulating the gene that encodes CETP. The microbial fermentation product is a composition chosen from the group consisting of PAZ, specific components isolated from PAZ, and chemically synthesized analogues of the components of PAZ as described above. The microbial fermentation product can be a liquid oral supplement, and other dosage forms and administration profiles can be used with this method as described herein. An assay can be performed to confirm that the up-regulating and down-regulating steps have been performed as previously described above.

The present invention further provides for a method of preventing the onset of high cholesterol by administering an effective amount of a composition chosen from the group consisting of PAZ, specific components isolated from PAZ, and chemically synthesized analogues of the components of PAZ, regulating genes involved in lipoprotein metabolism, and preventing the onset of high cholesterol. This is a prophylactic method in which individuals who are at risk for developing high cholesterol can take measures to protect themselves. Once an individual is confirmed to be at risk of developing high cholesterol, they can begin to take the composition. The composition can be administered daily. The composition can be in the form of a liquid oral supplement, a nutraceutical, or food additive. Any other dosage form or administration regimen can be used.

In the Examples below, various tests have been performed with PAZ and fractions thereof to determine gene regulation and cholesterol levels. A similar pattern of gene regulation is observed for animals treated with certain chromatographically purified fractions (e.g. fraction PF3 and PF4) that contain relatively few components as compared to PAZ itself. However, expression of the gene encoding ApoA1 is more markedly enhanced by PAZ than by PF3 or PF4 alone, indicating the presence in PAZ of additional component(s) with beneficial effects on cholesterol metabolism, or synergistic effects of components in these two fractions. Therefore, more generally, high cholesterol levels can be beneficially treated using PAZ or compounds contained therein to up-regulate ApoA1, and/or SRB1, and/or down-regulate CETP.

PAZ and PF4 have been tested for direct effects on the functional activity of the proteins CETP and HMGCoA reductase, and found to have no effect. This data further supports the mechanism being at the transcriptional level (see Example 2).

In contrast to the demonstrated ability of PAZ and components of PF3 and PF4 to favorably alter the expression of one or more of these three genes in vivo, when they were tested for their ability to influence the expression of genes involved in cholesterol metabolism in cultured human liver cells (HepG2), only significant change in the expression of the gene encoding CETP was observed. When tested in vitro on vascular epithelial cells (HUVEC), the results obtained were erratic and inconsistent with the observed beneficial effect on cholesterol metabolism in vivo. Hence the observed activity is unobvious in that, when approached using the methods employed in modern pharmaceutical research, namely screening first in vitro on cell lines, PAZ would be excluded from further consideration as a cholesterol lowering composition (See Example 3).

The overall effect of PAZ, as shown in Example 1, is that it decreases total plasma cholesterol (TC) as well as LDL. PAZ also significantly increases HDL, which produces an improved TC/HDL ratio. The change in plasma cholesterol is also accompanied by a shift in lipoprotein particles. Each of these effects is produced by the up-regulation and/or down-regulation of the expression of specific genes as described above.

While experiments were performed in hamsters with the compounds of the present invention, the results are predictive of those expected in humans. Hamsters are a preferred model for use in predicting the efficacy of candidate drugs on cholesterol metabolism in humans.

PAZ, or preparations or compounds derived therefrom, can be administered daily, or according to a dosing regimen deemed appropriate by a physician. This treatment can be provided as a therapeutic regimen to a patient who has been diagnosed with unhealthy cholesterol levels in order to bring their cholesterol to more desirable levels. Alternatively, the treatment can be provided as a preventative regimen to a patient who has a propensity to develop high total and LDL cholesterol levels and low HDL cholesterol levels due to a variety of factors, and in this instance PAZ can be administered as a prophylactic treatment.

PAZ can also be administered as a nutraceutical or a food additive in various drinks or other food substances.

The PAZ, fractions derived therefrom, or compounds synthesized that are equivalent or analogues of the active components of PAZ, which are the subjects of the present invention are administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compounds of the present invention can be administered in various ways. It should be noted that it can be administered as the compound and can be administered alone or as an active ingredient in combination with pharmaceutically acceptable carriers, diluents, adjuvants and vehicles. The compounds can be administered orally, subcutaneously or parenterally including intravenous, intraarterial, intramuscular, intraperitoneally, intratonsillar, and intranasal administration as well as intrathecal and infusion techniques. Implants of the compounds are also useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

The doses can be single doses or multiple doses over a period of several days. The treatment generally has a length proportional to the length of the disease process and drug effectiveness and the patient species being treated.

When administering the compounds of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, can also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

The invention is further described in detail by reference to the following experimental examples. These examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein.

Example 1

The specific aim of this experiment was to employ chromatographic techniques separate the complete PAZ culture filtrate into fractions based on the chemical and physical properties of its components in order to (a) determine if the biological activity required the complete complex mixture or was due to one or a few of its components, (b) evaluate the biological activity of each of the PF fractions derived by this process in both in vitro (cell culture) and in vivo (hamster) experimental model systems.

Materials and Methods

The following assay kits were used for the plasma cholesterol analysis:

From Pointe Scientific:
Cholesterol Liquid (C7510—for plasma total cholesterol)
Triglyceride GPO Liquid Reagent set (T7531—for plasma TG)
HDL/Cholesterol Mg/Dex (H7507—for plasma HDL by Magnesium precipitation)

From Wako:
Free Cholesterol E (435-35801)
Phospholipids C (433-36201)

ProAlgaZyme™ was separated into subfractions.
F1: weak anion exchange to capture most proteins
F2: strong anion exchange to capture molecules containing carboxyl groups and other negatively charged functionalities, as well as negatively charged ions
F3: strong cation exchange to capture molecules containing amino groups and other positively charged functionalities, as well as positively charged ions
Column 4 a C18 derivatized column that binds non-polar organic molecules
F4: The liquid that flows through (does not bind) to any of the series of resins employed (weak anion exchange, strong anion exchange column, strong cation exchange, and C-18 column). This "flow though" fraction is called PF4, contains relatively few molecules, which should include polar but uncharged organic molecules, as well as molecules of low polarity that were not captured by column 4 and was also evaluated for biological function.

The Study Design is shown in FIG. 1:
HF: High Fat Diet (30% calories from fat; primarily coconut oil containing saturated fatty acids+1% soybean oil)
PAZ: ProAlgaZyme™ (complete solution)
PF1, PF2, PF3, and PF4 are chromatographically separated
Fractions of PAZ
The control animals were fed regular hamster diet.
P: refers to high fat diet (30% calories from coconut oil)
PW: High Fat Diet+Water
PP: High Fat Diet+complete ProAlgaZyme™ (diluted 20 ml in 100 ml)
PF1: High Fat Diet+fraction 1 of ProAlgaZyme™ (diluted 5 ml in 100 ml)
PF2: High Fat Diet+fraction 2 of ProAlgaZyme™ (diluted 5 ml in 100 ml)
PF3: High Fat Diet+fraction 3 of ProAlgaZyme™ (diluted 5 ml in 100 ml)
PF4: High Fat Diet+fraction 4 of ProAlgaZyme™ (diluted 20 ml in 100 ml)
p value=statistical significance with respect to PW. (One way ANOVA, STATPLUS); n=10/group
$p<0.05$ implies that the mean value of the parameter (e.g. TC) between the two groups being compared are statistically different. The lower the p value, the higher the statistical significance.

On the graphs, columns which are statistically different as compared to PW have been indicated by * ($p<0.05$) or ** ($p<0.01$)

Summary:
Preventative Effect of PAZ on Plasma Lipids in a Hamster Cholesterolemia Preventative Model System PAZ provides a statistically significant decrease in total plasma cholesterol (TC) and non-HDL (LDL) over the 28 day preventative study. PAZ provides a statistically significant increase in HDL, leading to a marked improvement in the TC/HDL ratio. Change in plasma cholesterol is accompanied with a shift in lipoprotein particles. Results are shown in FIGS. 2-12.

Figure 2:
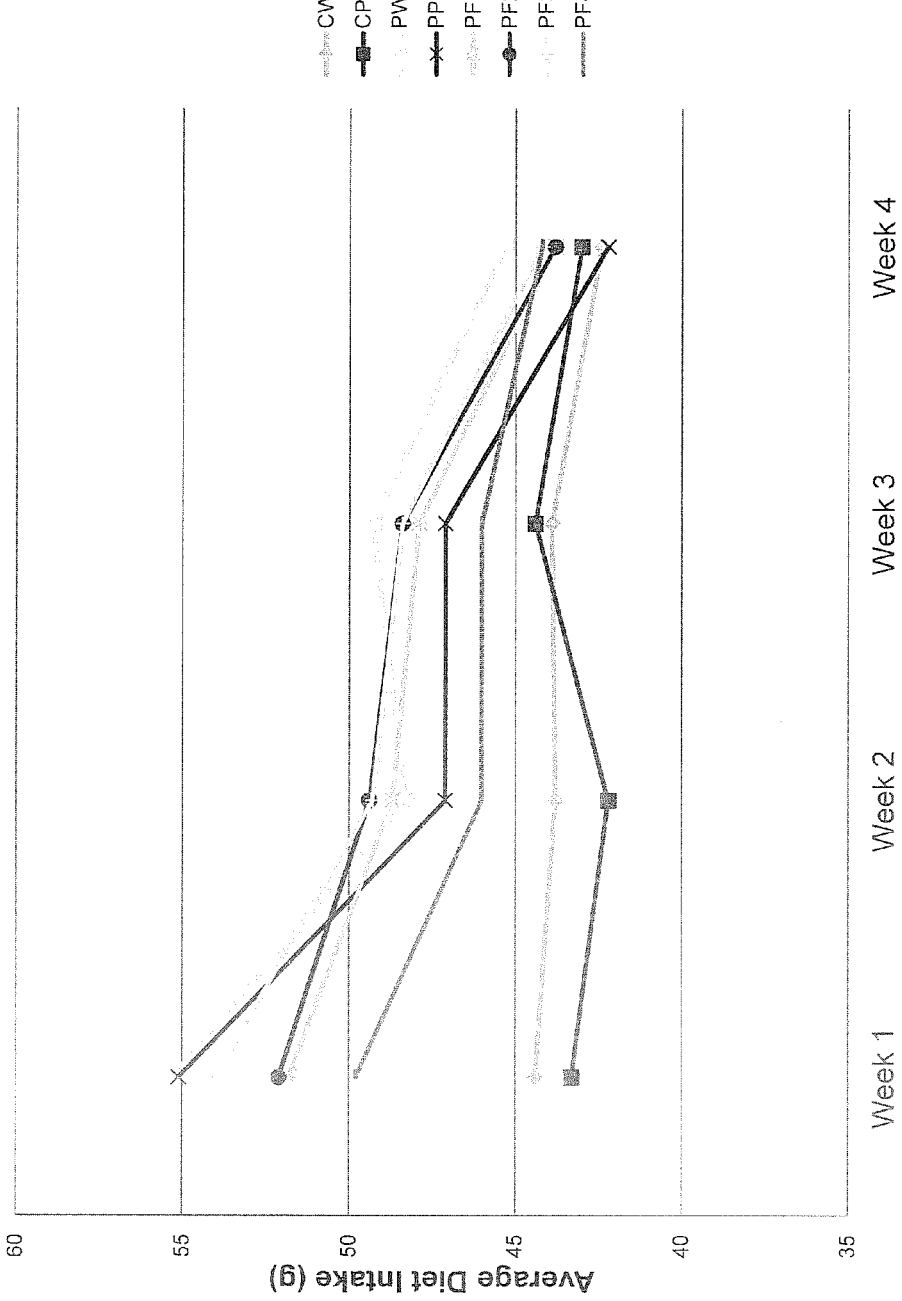
FIG. 2 is a graph of the average dietary intake of high fat food in grams for hamsters provided with water and hamsters provided with water containing PAZ or fractions isolated therefrom (see FIG. 1 for legend)
Figure 3:
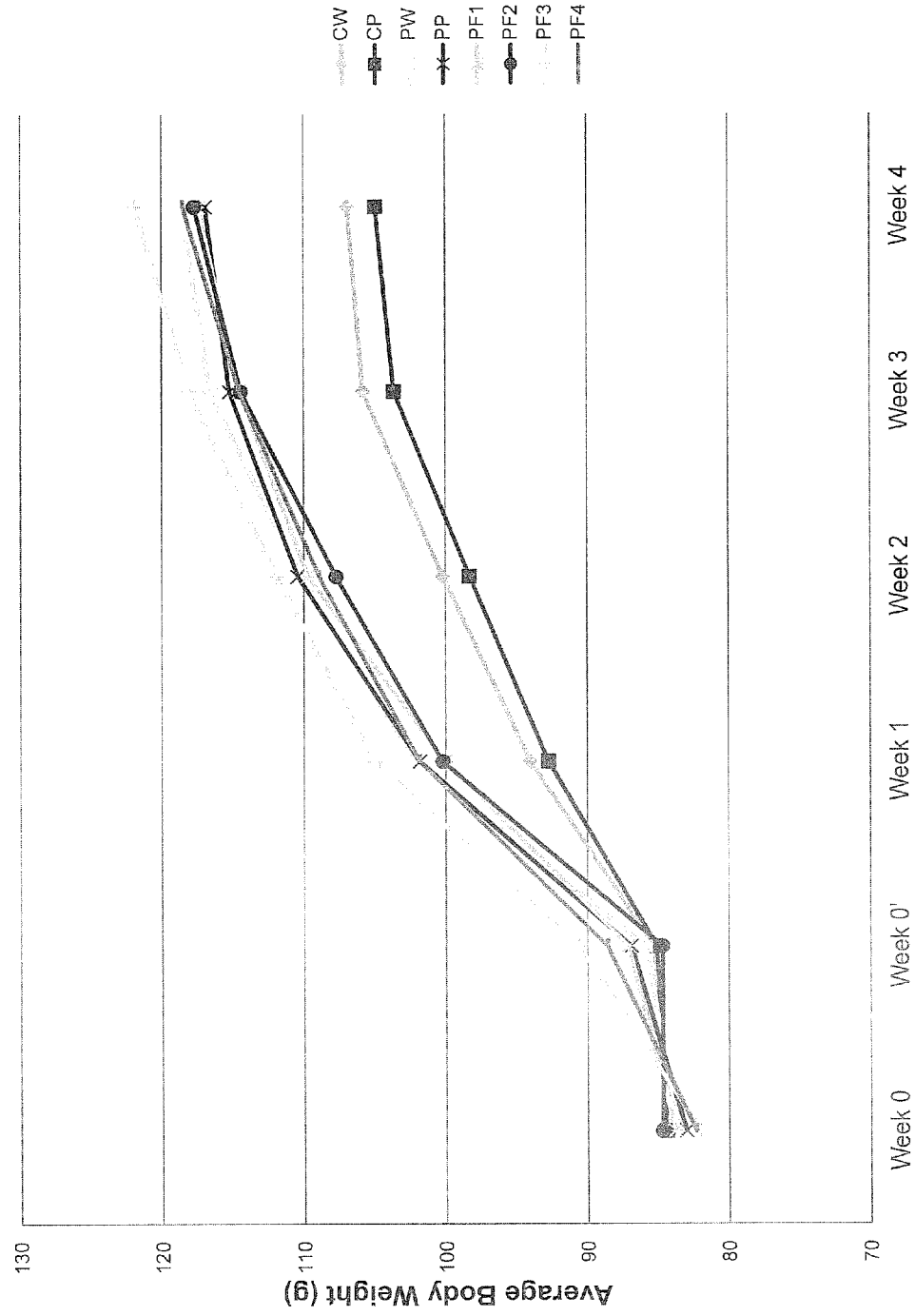
FIG. 3 is a graph of average body weight (grams) over the course of the study (weeks) for hamsters provided with water and hamsters provided with water containing PAZ or fractions isolated therefrom (see FIG. 1 for legend)
Figure 4:
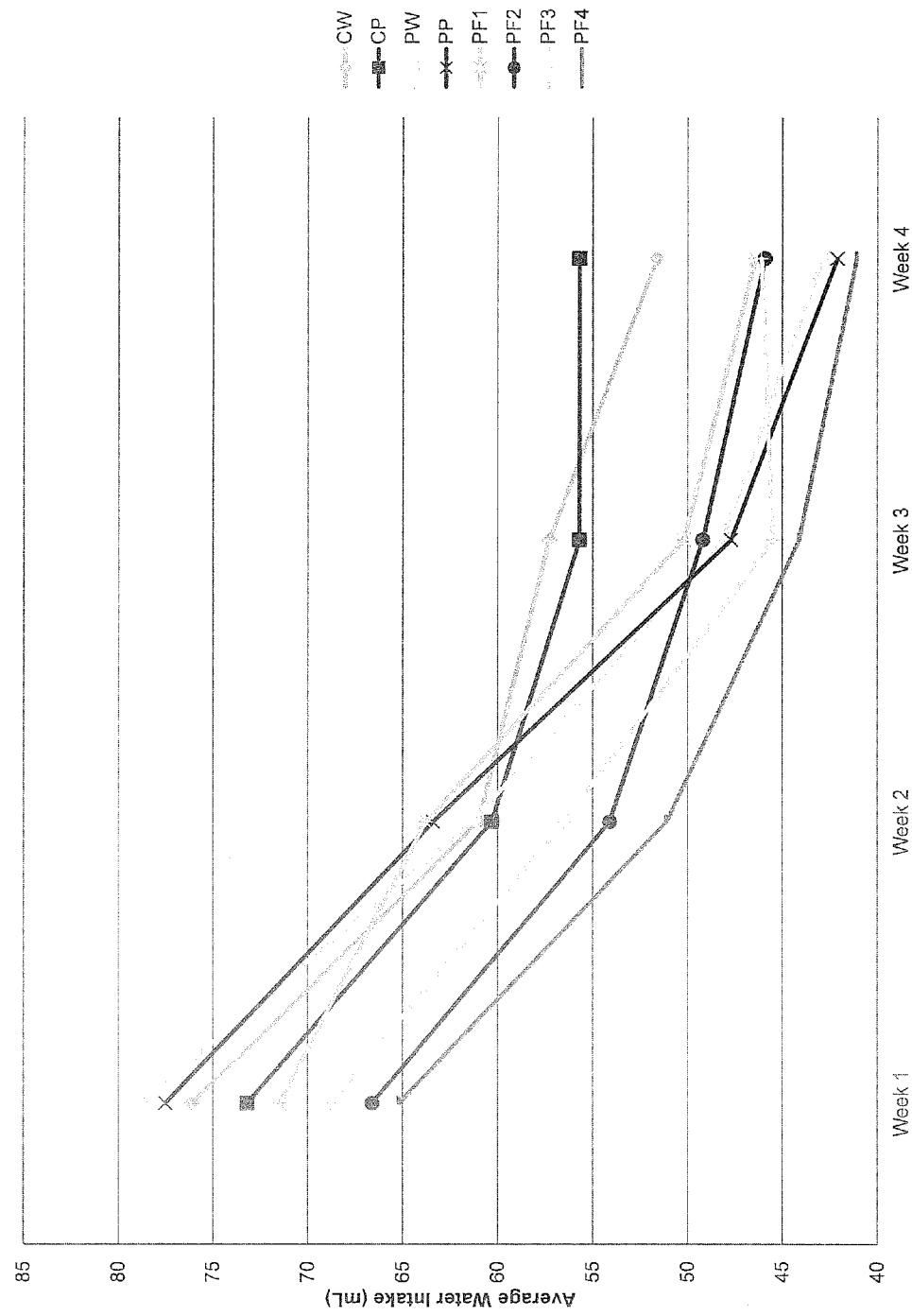
FIG. 4 is a graph of average fluid intake (mL) over the course of the study for hamsters provided with water and hamsters provided with water containing PAZ or fractions isolated therefrom (see FIG. 1 for legend)
Figure 5:
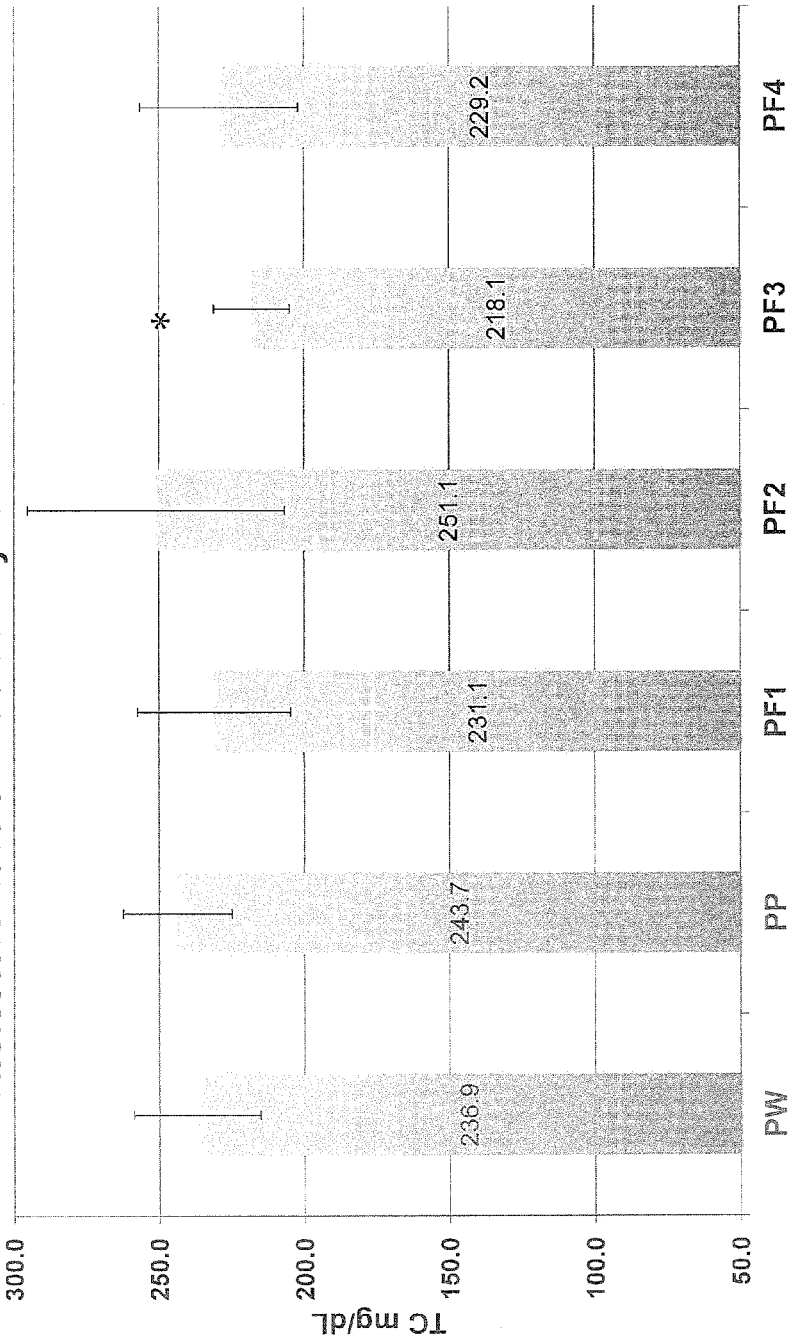
FIG. 5 is a graph of the effects of PAZ and fractions isolated therefrom compared to water without any additives on total cholesterol levels (mg/dL) of hamsters fed a high fat diet.
Figure 6:
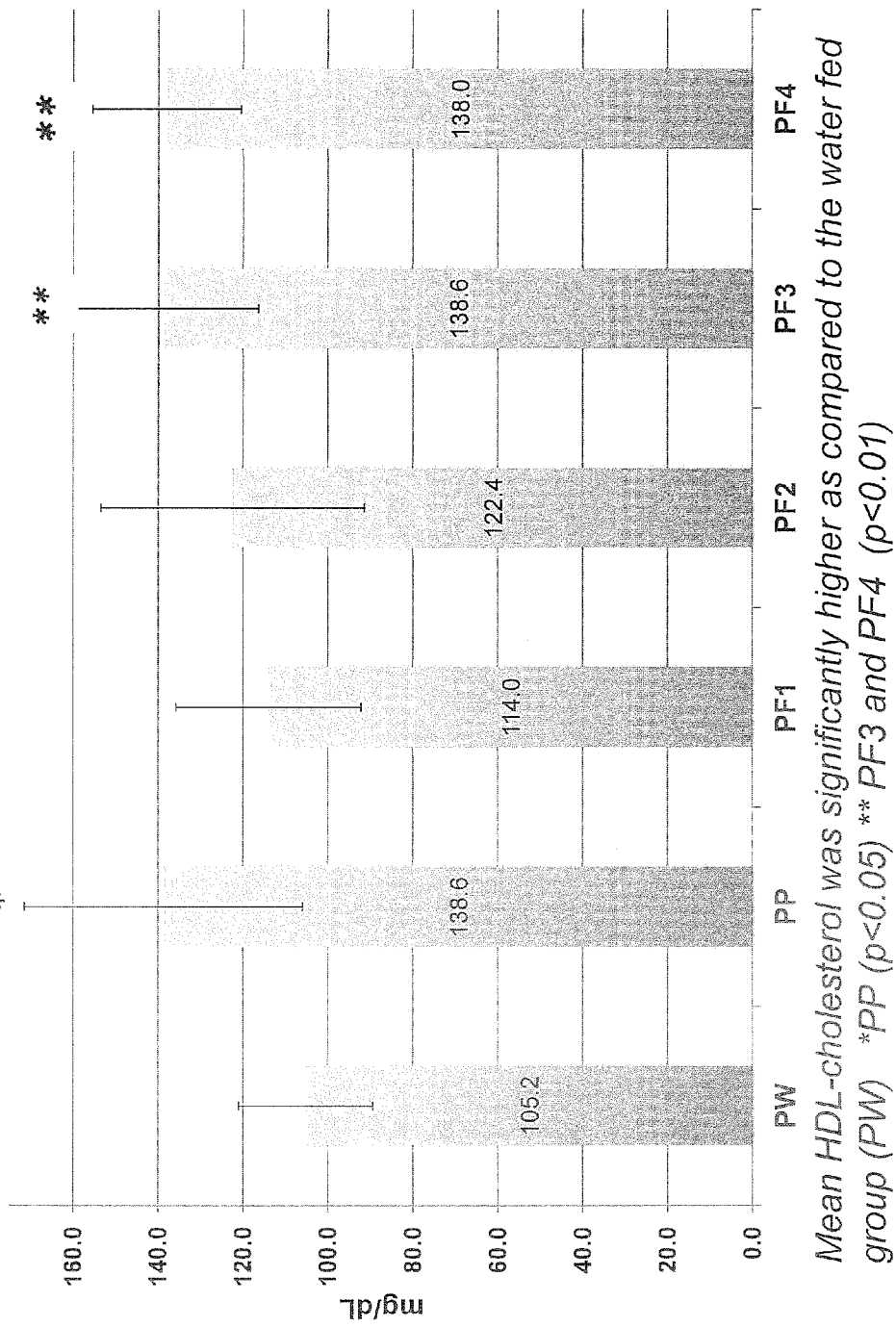
FIG. 6 is a graph of the effects of PAZ and fractions isolated therefrom compared to water without any additives on HDL-cholesterol levels (mg/dL) of hamsters fed a high fat diet.
Figure 7:
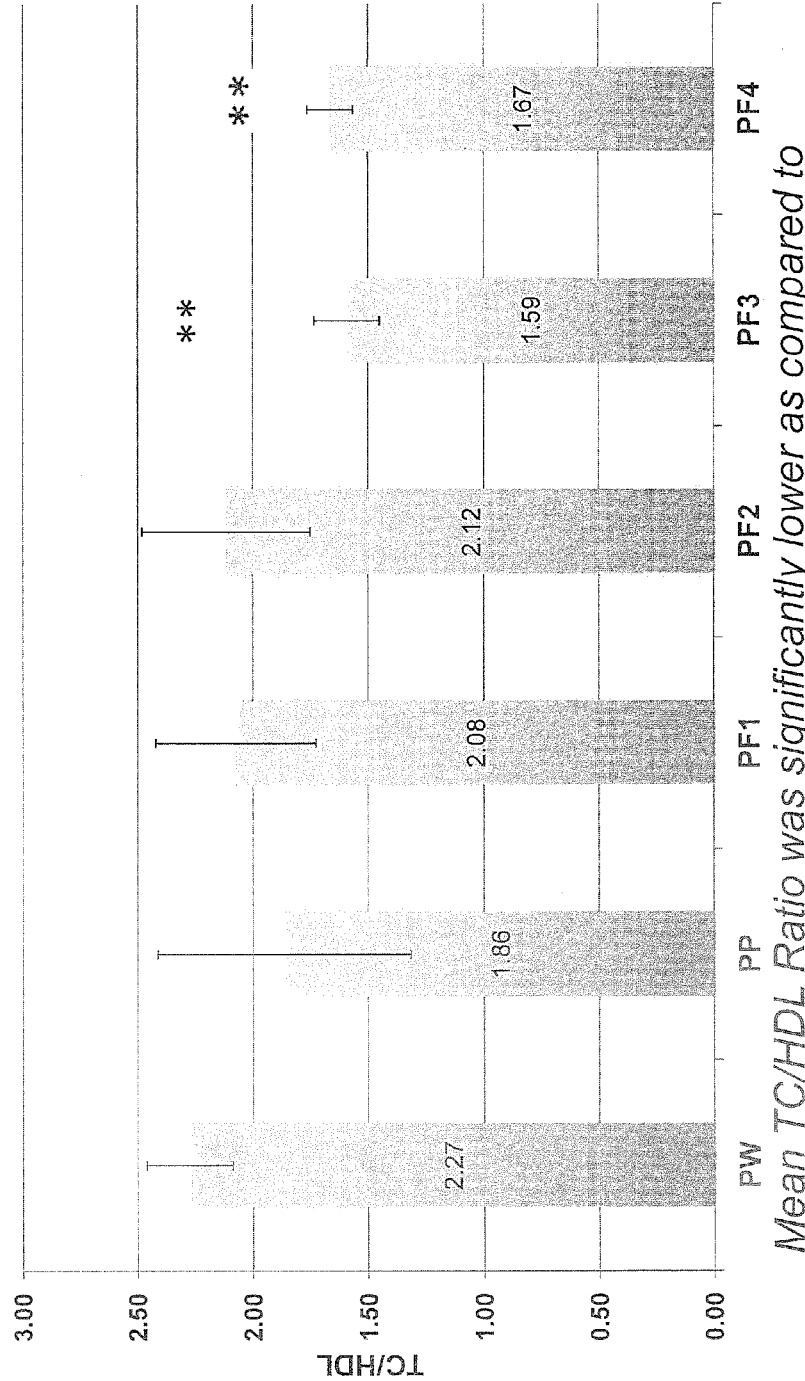
FIG. 7 is a graph of the effects of PAZ and fractions isolated therefrom compared to water without any additives on the ratio of total and HDL cholesterol levels of hamsters fed a high fat diet.
Figure 8:
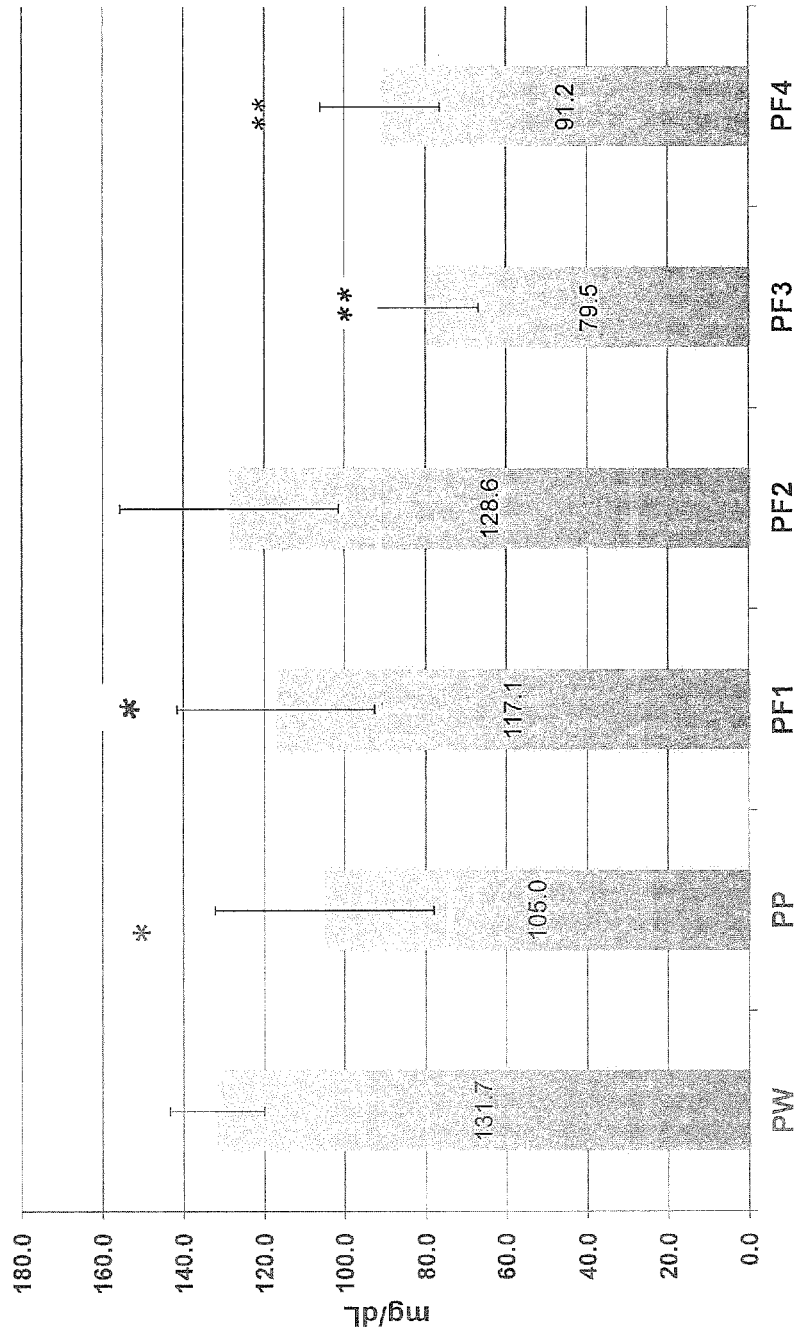
FIG. 8 is a graph of the effects of PAZ and fractions isolated therefrom compared to water without any additives on non-HDL (LDL) cholesterol levels (mg/dL) of hamsters fed a high fat diet.
Figure 9:
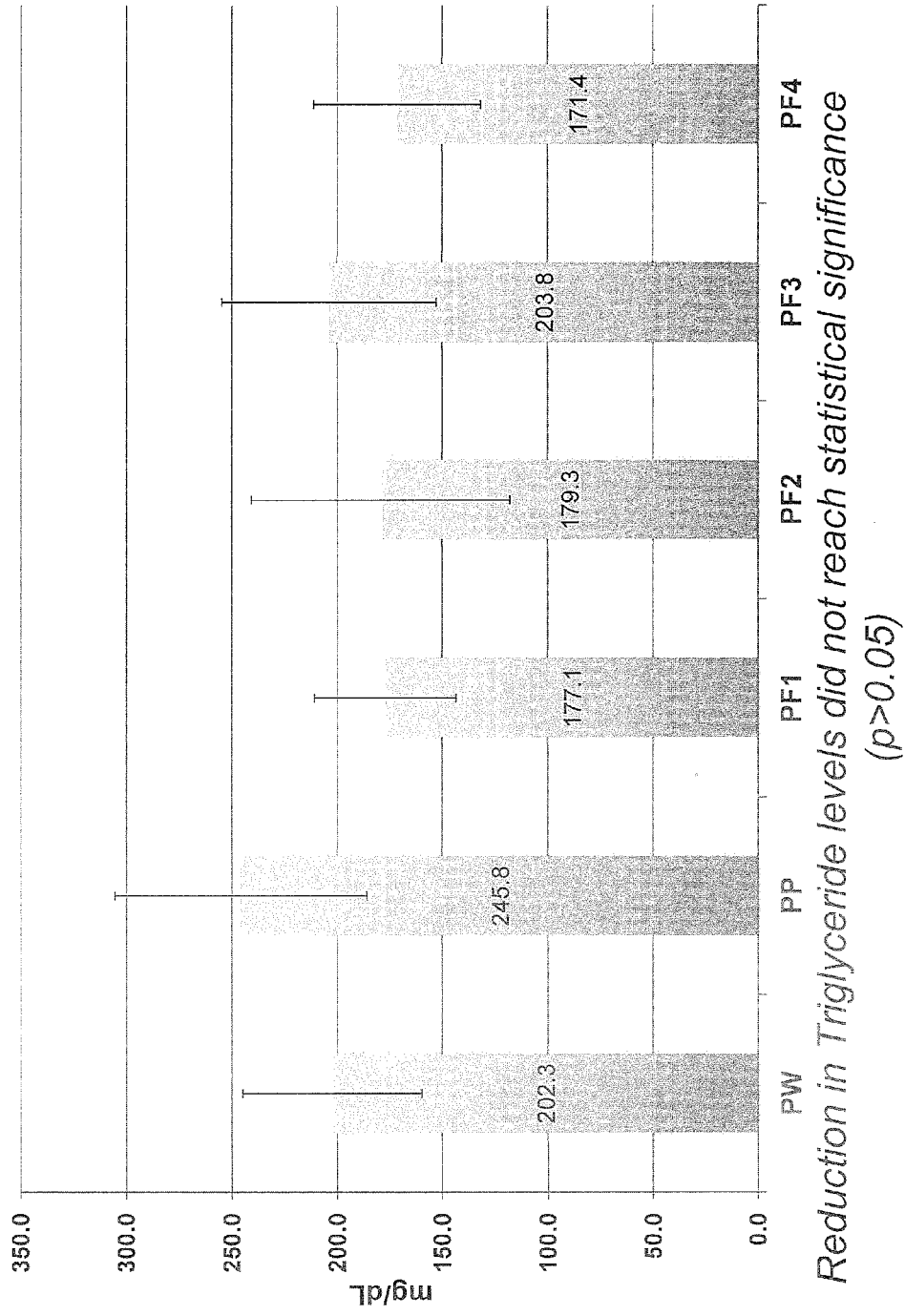
FIG. 9 is a graph of the effects of PAZ and fractions isolated therefrom compared to water without any additives on plasma triglyceride levels (mg/dL) of hamsters fed a high fat diet.
Figure 10:
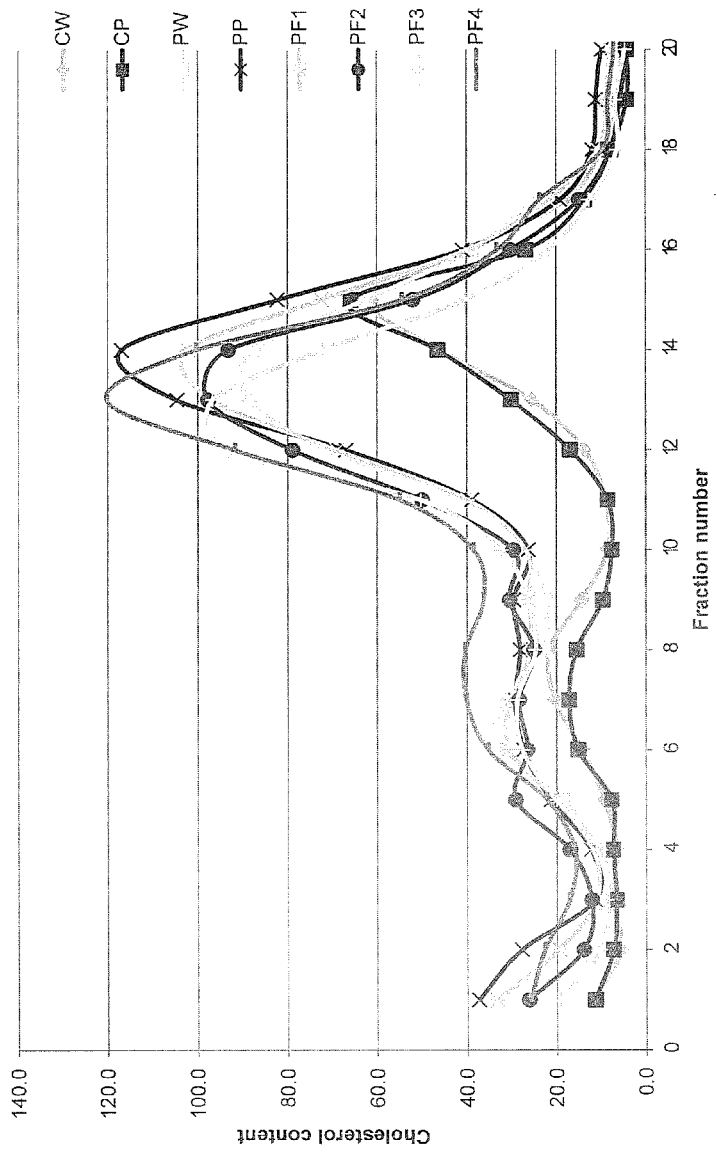
FIG. 10 is a graph of the effects of PAZ and fractions isolated therefrom compared to water without any additives on the lipoprotein profile of hamsters fed a high fat diet.

As shown in FIG. 2, average diet intake generally decreased over four weeks. As shown in FIG. 3, average body weight increased over four weeks. FIG. 4 shows that average water intake decreased over four weeks. FIG. 5 shows that mean TC was significantly lower for PF3 fed animals than for animals given water (PW). FIG. 6 shows that mean HDL cholesterol was significantly higher for PP, PF3, and PF4 as compared to the water fed group (PW). FIG. 7 shows that mean TC/HDL ratio was significantly lower for PF3 and PF4 as compared to PW. FIG. 8 shows that mean LDL cholesterol was significantly reduced for PP, PF3, and PF4 as compared to PW. FIG. 9 shows that reduction in triglyceride levels did not reach statistical significance. FIG. 10 shows the lipoprotein profile of each group, and each PAZ composition produced a shift in the profile.

Figure 11:
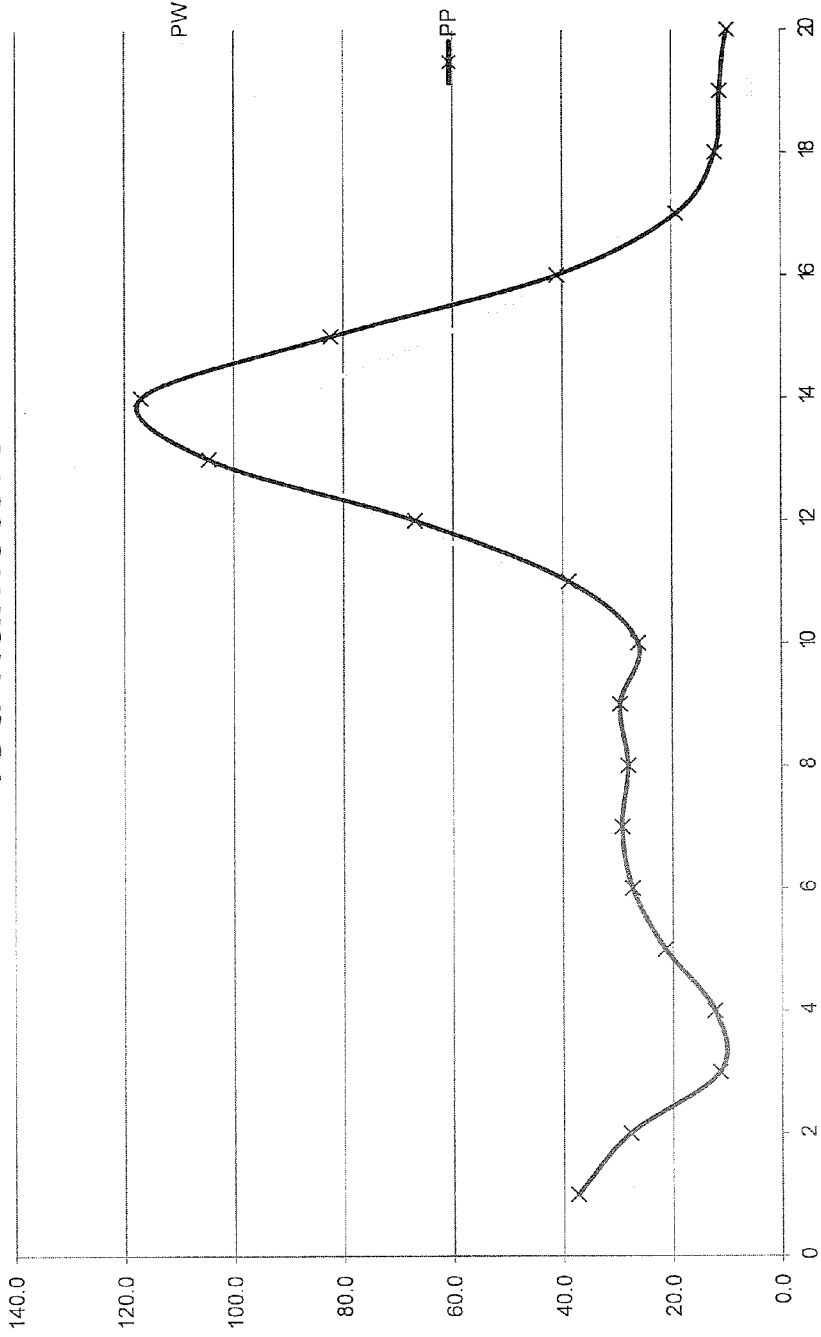
FIG. 11 is a graphical representation of the shift in lipoprotein composition for hamsters fed a high fat diet plus PAZ and fractions isolated therefrom compared to hamsters fed a high fat diet plus water without any additives.
Figure 12:
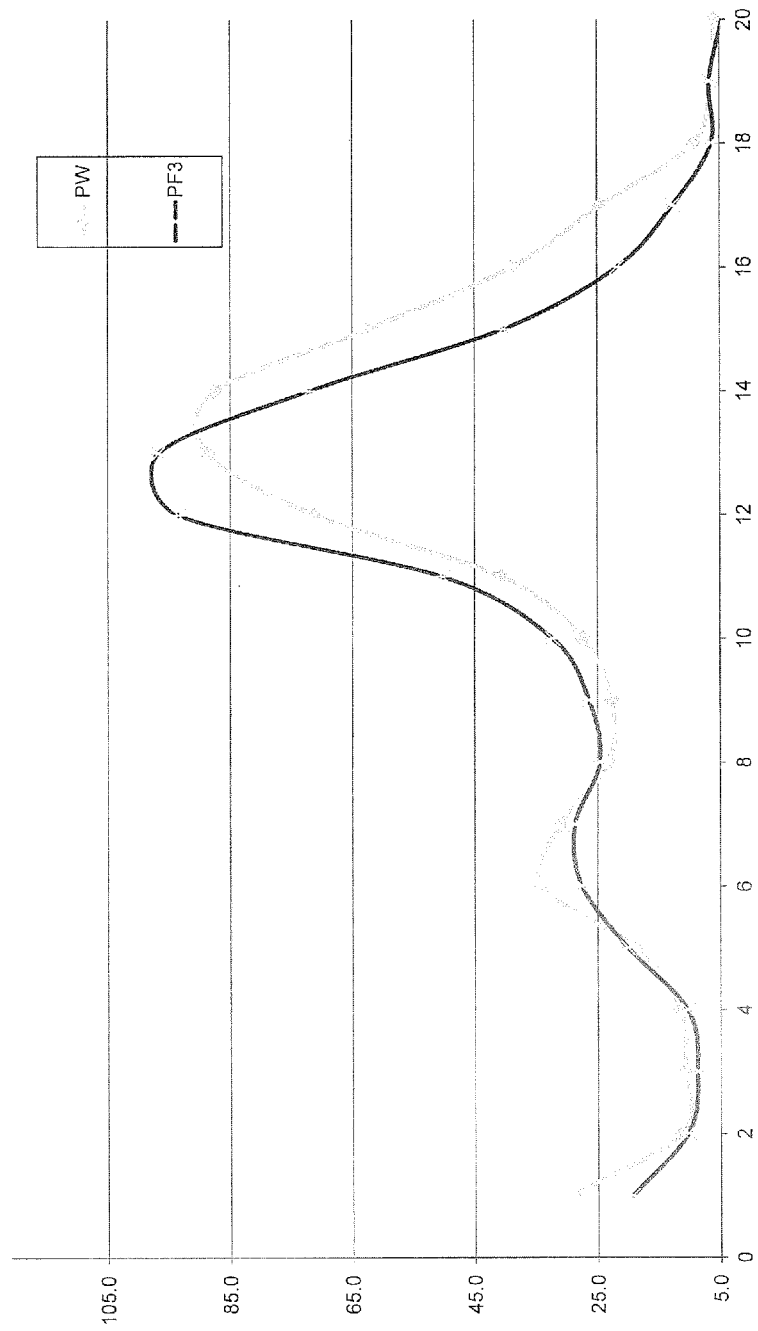
FIG. 12 is a graphical representation of the shift in lipoprotein composition for hamsters fed a high fat diet plus the PF3 fraction of PAZ compared to hamsters fed a high fat diet plus water without any additives.

FIG. 11 shows that there was a shift in lipoprotein composition from lower to higher density particles between hamsters fed water (PW) and those fed complete ProAlgaZyme™ (PP). FIG. 12 shows that there was a shift in lipoprotein composition from lower to higher density particles in water versus PF3 fed hamsters.

The aims of the experiments described in Example 2 were (a) to test the activity of PAZ and its fractions to for their ability to alter the function of key proteins involved cholesterol metabolism and, if such a mechanism (which is for example the case for statins) was identified, (b) to employ such assay(s) to facilitate further fractionation of the PAZ extract and ultimate characterization of active component(s).

Example 2

This example details the qualitative analysis of the effects PAZ filtrates PF4 and PF3 have on the enzyme activity of cholesterol metabolizing enzymes Cholesteryl ester transfer protein (CETP), Phospholipid transfer protein (PLTP) and HMG-CoA Reductase (HMGR).

Procedure:
CETP and PLTP Assays:
CETP Inhibitor Drug Screening Kit (Catalog #K602-100) and PLTP Inhibitor Drug Screening Kit (Catalog #K602-100) were obtained from BioVision Research Products (Mountain View, Calif.). The enzyme assays were carried out according to the manufacturer's instructions. Briefly, 160 µl of deionized (DI) water, PF4 (undiluted) or PF3 (diluted 1:10 in DI water) was dispensed into wells of a black 96-well microtiter plate. Varying volumes of control rabbit serum (source of CETP and PLTP) were then added to the wells. Some wells did not receive serum and served as background fluorescence (blank) controls. A Master Mix consisting of 1 part Acceptor Molecule solution, 1 part Donor Molecule solution and 2 parts 10× Assay Buffer per well was prepared and scaled up to the number of wells used in each assay. Forty µl of Master Mix was added to each well, the plate sealed and incubated at 37° C. in a humidified chamber for 45 minutes. The fluorescence intensity of each well was measured using a Labsystems Fluoroskan Ascent FL fluorometer with a 485 nm excitation and 527 nm emission filter pair. Each condition was performed in duplicate with the averages reported (standard deviation error bars are applied to each average).

HMGR Assay:
HMG-CoA Reductase (HMGR) Assay Kit was obtained from Sigma-Aldrich (St. Louis, Mo.). The enzyme assay was carried out according to the manufacturer's instructions. Briefly, 1.5 ml microfuge tubes had the following reagents added to them in this order: 1× Assay buffer, inhibitor (either the supplied Pravastatin inhibitor, PF4 (15 µl) or PF3 (15 µl of a 1:10 dilution) to the inhibitor control and test samples), NADPH, HMG-CoA Substrate Solution, and HMGR. One tube did not have HMGR added and was used as the blank. The positive control sample contained HMGR but no inhibitor. All reactions were carried out in 1 ml volumes. Tubes were briefly vortexed after addition of HMGR to mix prior to transferring reaction solutions to UV-Visible cuvettes. Absorbance readings at 340 nm were taken every 15 seconds for 5-7 minutes in a Shimadzu UV-1601 UV-Visible spectrophotometer. The absorbance readings at 340 nm will decrease in samples with enzymatic activity (e.g. positive control sample) due to the decrease in NADPH concentration.

Results:
CETP and PLTP Assays:
There was no significant effect on CETP (FIG. 13) or PLTP (FIG. 14) enzyme activity by PF4 when compared to the activity of these enzymes in DI water at the volumes of serum used.

Figure 15:
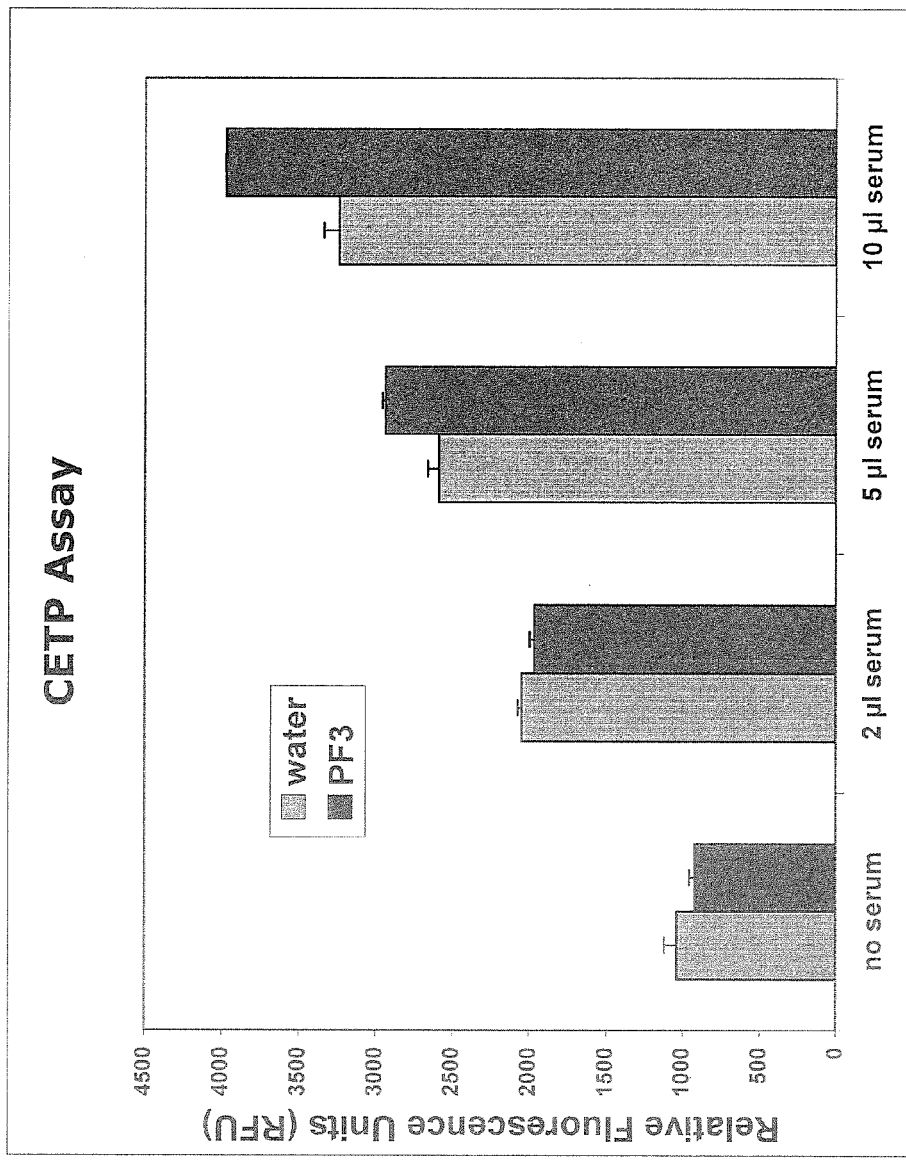
FIG. 15 is a graphical representation of the results obtained for assays of CETP activity in blood serum to which either water or PF3 (at a 1:10 dilution) were added.
Figure 16:
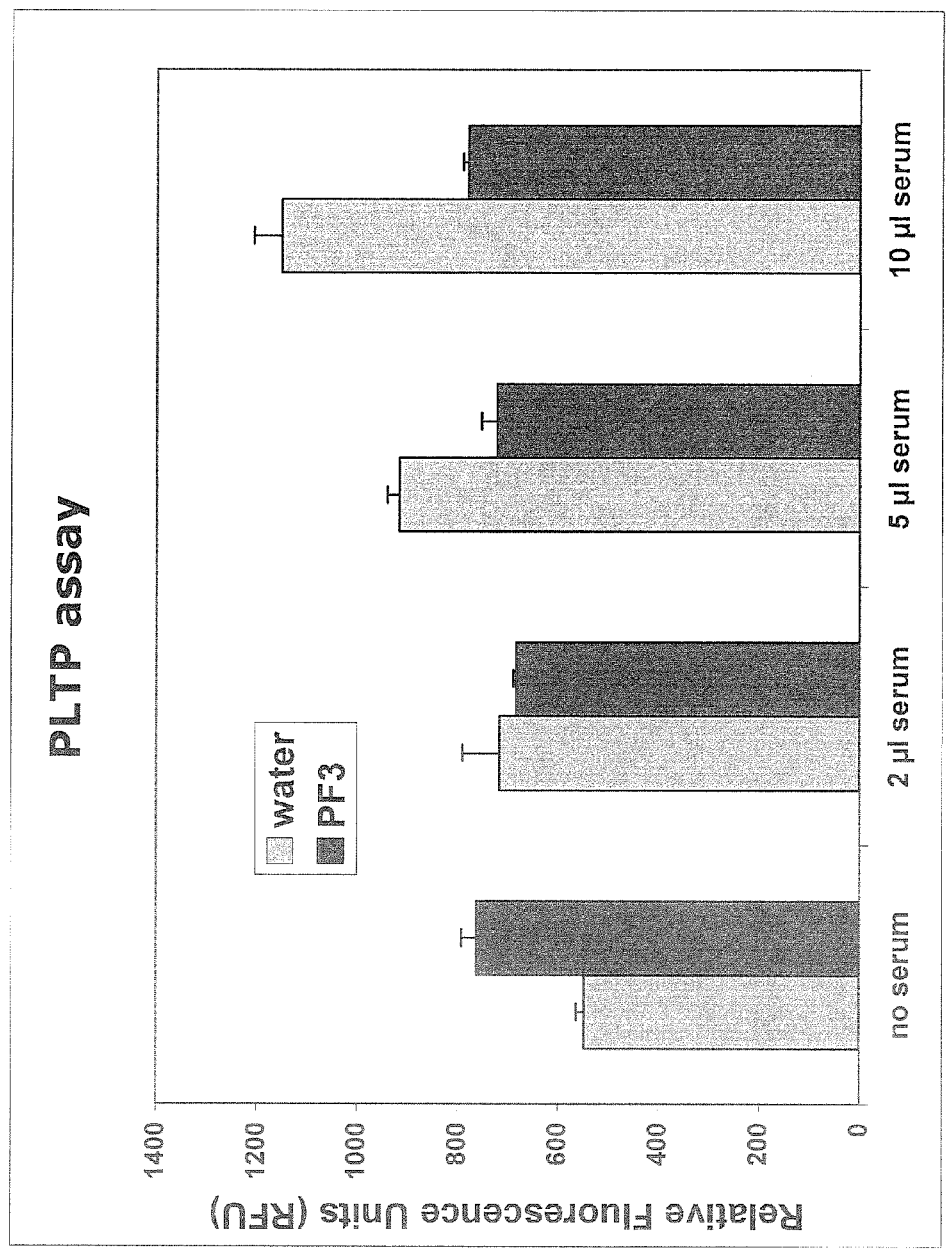
FIG. 16 is a graphical representation of the results obtained for assays of PLTP activity in blood serum to which either water or PF3 (at a 1:10 dilution) were added.

A slight augmentation in CETP activity is observed in the presence of PF3 (diluted 1:10) at higher amounts of serum (FIG. 15) (see Conclusions). PF3 appeared to have a negative, or inhibitory, effect on PLTP activity compared to DI water (FIG. 16).

Figure 17:
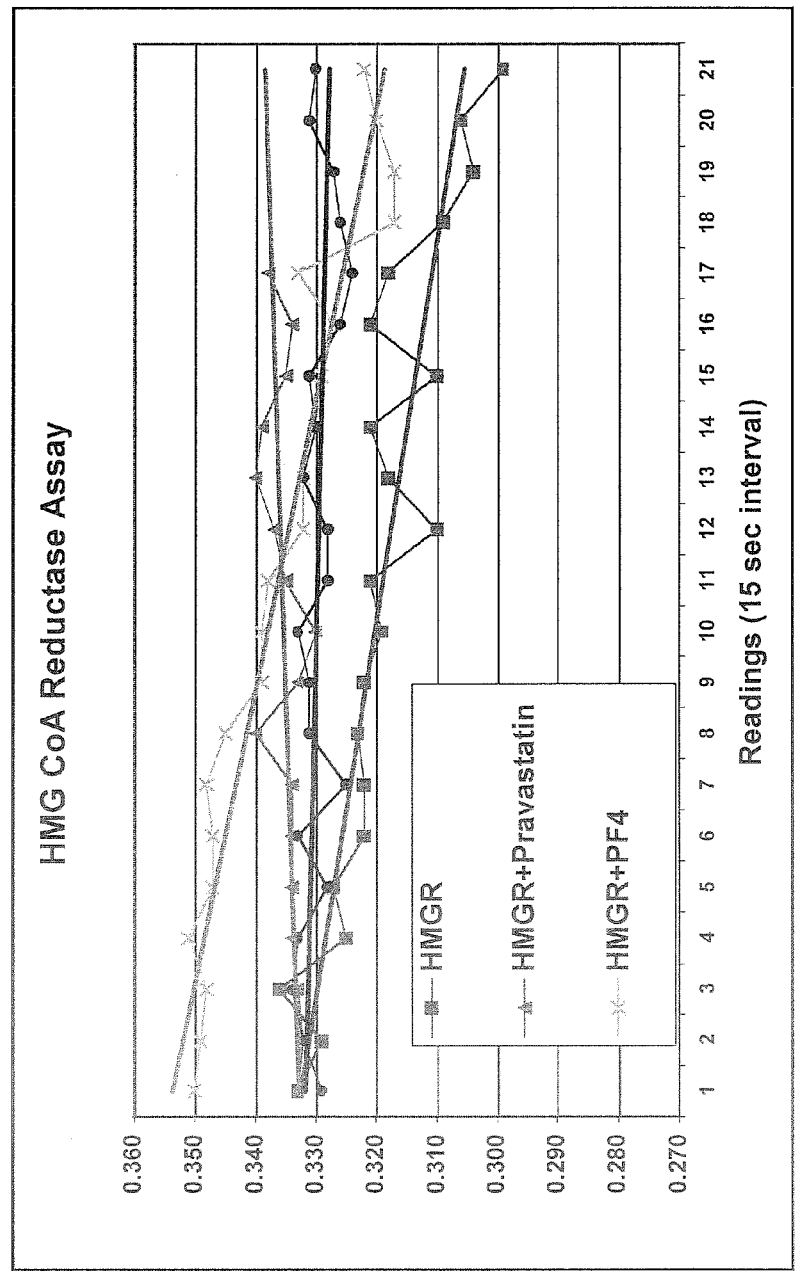
FIG. 17 is a graphical representation of a kinetic assay comparing the effect on HMGCoA Reductase activity of a statin (prevastatin) vs. fraction PF4 derived from PAZ.
Figure 18:
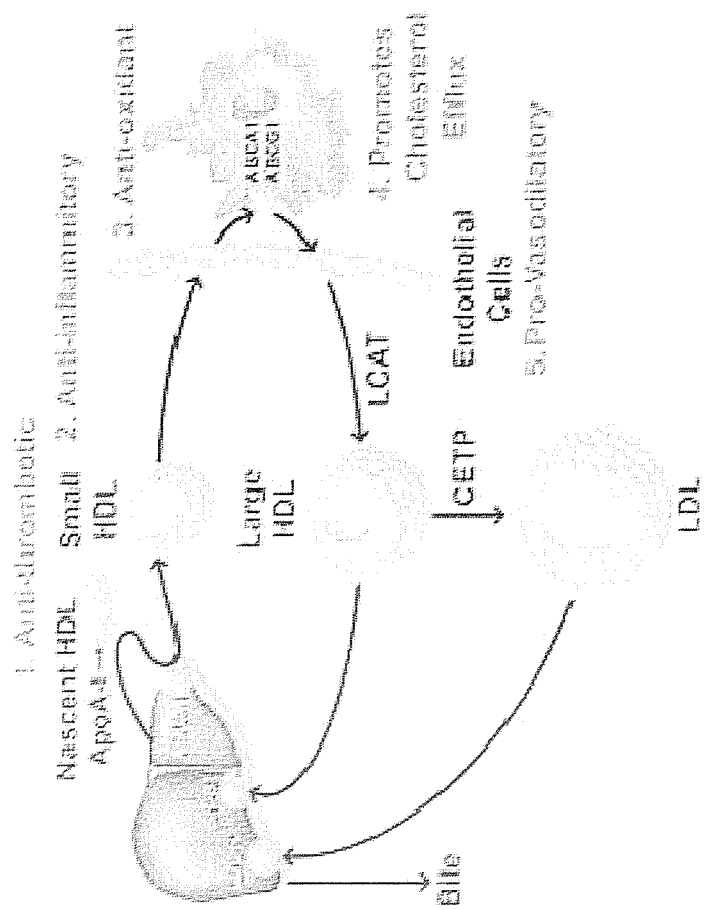
FIG. 18 is a depiction of the role of various proteins and lipoproteins in cholesterol transport.

HMGR Assay:
Without any inhibitor present, HMGR enzyme activity produces an appreciable downward (negative) slope (FIG. 17, solid pink trend line). As expected, HMGR activity in the presence of the inhibitor pravastatin was significantly reduced (FIG. 17, compare the solid pink trend line (HMGR) with the solid orange trend line (HMGR+pravastatin)). A decrease in HMGR activity was not detected when PF4 was present in the assay (FIG. 17, compare solid pink trend line (HMGR) with the solid light blue trend line (HMGR+PF4)). However, PF3 was observed to have an inhibitory-like effect on HMGR activity in this assay (FIG. 17, compare the solid pink trend line (HMGR) with the purple trend line (HMGR+PF3)).

Conclusions:
CETP and PLTP Assays:
Fold increases in control fluorescence values (assay measurements obtained using DI water with or without control serum) were within the anticipated range as reported in the manufacturer's instructions indicating that the assay was performing as expected.

PAZ fraction PF4 did not appear to have any effect on the activity of either CETP or PLTP using these assay kits. PAZ fraction PF3 (diluted 1:10) did appear to have an effect on the activity of CETP and PLTP. However, the effect is contrary to what was expected based on the mechanism of action of these two enzymes and the report of the cholesterol lowering potential of PF3 in an in vivo hypercholesterolemia model. Caution with the interpretation of this data, especially for PF3, is thus warranted. Although PF3 was diluted 10-fold in DI water in these assays, there is still a significant amount of salt present compared to DI water alone or PF4. This could have an adverse effect on the activity of the enzymes tested for or the fluorescently labeled lipid used in the assays. In addition, the pH of diluted PF3 was not examined prior to use in these assays, which can also contribute to the same adverse affects. One other important aspect of this study is showing that PAZ does not act directly on lipoproteins and therefore does not have the same mechanism of action as statins that are currently used to treat high cholesterol.

HMGR Assay:
In this activity assay, a decrease in absorbance at 340 nm over time indicates HMGR activity as the NADPH concentration decreases due to its conversion to NADP by HMGR. PAZ fraction PF4 did not appear to inhibit HMGR activity in this assay. However, there was an observable inhibition noted for PAZ filtrate PF3. Again, caution should be taken when interpreting these results for the same reasons as given for the observed effects of PF3 on CETP and PLTP activity.

It was previously disclosed that PAZ fractions would be evaluated for their affect on four enzymes involved in cholesterol metabolism. Assays were performed and preliminary data was obtained for CETP, PLTP and HMG-CoA Reductase as detailed above. The fourth enzyme, lecithin-cholesterol acyltransferase (LCAT; a major determinant of plasma HDL concentration) could not be evaluated. Based on the data above, it is concluded that there are no significant findings regarding direct effects of PF4 and PF3 on the activities of the CETP, PLTP and HMGR proteins.

Although these proteins, along with LCAT, are often the prominent targets evaluated when testing effects of pharmaceutical candidates on HDL-cholesterol levels, other mechanisms are involved in the reverse cholesterol transport pathway that leads to increasing HDL-cholesterol levels and should also be considered for evaluation at this time. For instance, ApoA1 constitutes 70% of the protein component of HDL particles and is present in nearly all HDL particles. Many researches believe that the best way to raise HDL-cholesterol levels is to produce more ApoA1, which is the precursor of new HDL cholesterol. For this reason the up-regulation of endogenous apoA-1 protein expression is considered one of the most promising approaches to the development of new therapies targeted to HDL cholesterol. Additional mechanisms that should be considered are the regulation of the membrane proteins, scavenger receptor class B, type 1 (SR-B1) and ATP-binding cassette 1 (ABC1) (the former as a bona fide receptor for HDL and the latter as a lipid transporter) as both have been strongly implicated as being important in cholesterol efflux. The regulation, and thus the availability, of LDL receptor expression and recycling is also a mechanism whereby cholesterol levels are physiologically adjusted and should be evaluated.

The data reveals little if any significant findings regarding the effects of fractions PF4 and PF3 on CETP, PLTP and HMGR activity. However, the same PAZ fractions used in the in vitro enzyme assays showed an ability to raise HDL-cholesterol levels in an in vivo animal hypercholesterolemia model. These apparently conflicting results could be due to (a) the mechanism involved in lowering cholesterol levels in vivo does not involve the specific enzymes we have tested in vitro, (b) an alternative mechanism such as alteration of the expression or turnover of one or more of these proteins, and/or (c) a requirement for an in vivo prebiotic conversion pathway acting on constituents in PAZ to generate an active metabolite. This bioactivation process can occur either within the gastrointestinal tract or blood stream of humans and animals or in the bacterial microflora that persists in the gut of humans and animals.

The aims of the experiments described in Examples 3 and 4 were (a) to evaluate PAZ and its fractions to for their ability to alter the expression of genes encoding key proteins involved cholesterol metabolism and, if such a mechanism was identified, (b) to employ such assay(s) to facilitate further fractionation of the PAZ extract and ultimate characterization of active component(s).

Example 3

One specific aim was to explain the more beneficial plasma lipid profile (lower TC, higher HDL) effected by feeding complete PAZ (PP) and fraction 4 of PAZ (PF4) to hamsters at the same time as a high fat diet (i.e. preventative model). Evaluation was therefore performed of the levels of expression of the genes involved in HDL metabolism of ApoA1, ABCA1, SR-B1, and CETP in tissues collected from hamster livers that were harvested after 4 weeks of the preventative protocol employed in Example 1. Another specific aim was to evaluate the effect of PAZ and its fractions on HDL gene regulation in vitro employing either HepG2 and HUVEC cell systems (data not shown). In this example, data is shown from five animals/groups with three replicates per animal.

Figure 13:
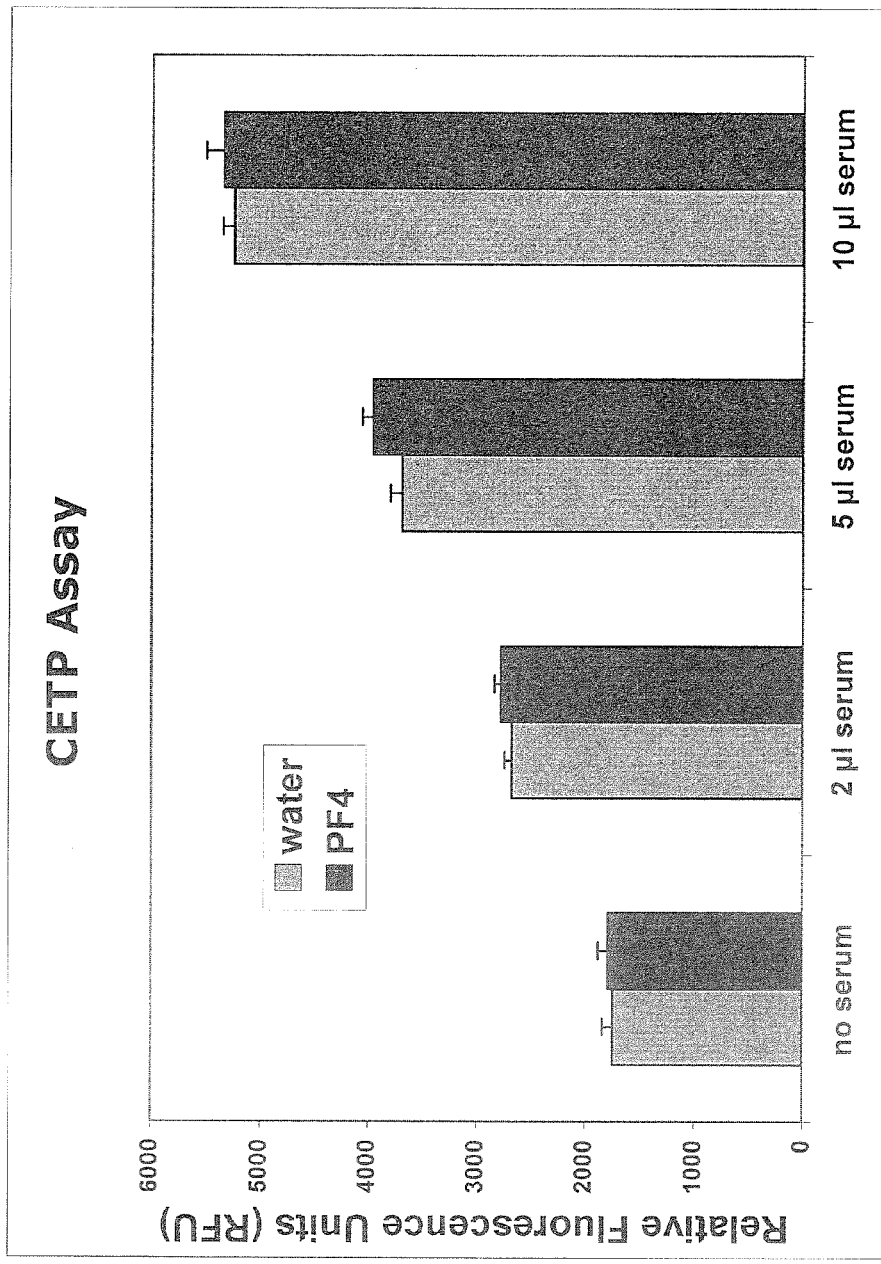
FIG. 13 is a graphical representation of the results obtained for assays of CETP activity in blood serum to which either water or undiluted PF4 were added.
Figure 14:
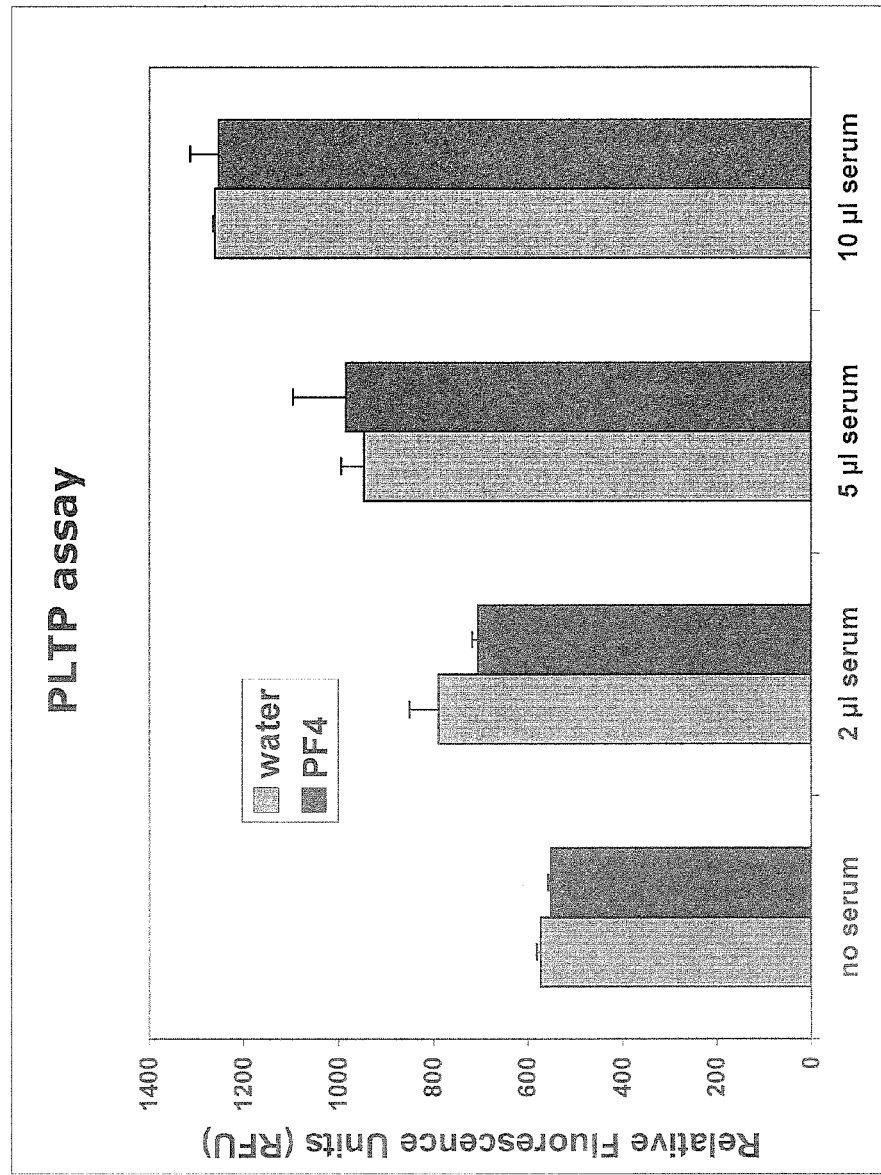
FIG. 14 is a graphical representation of the results obtained for assays of PLTP activity in blood serum to which either water or undiluted PF4 were added.

FIG. 13 illustrates major components of the reverse cholesterol transport pathway and other sites of HDL action on the pathogenesis of atherosclerosis factors. ApoA1 is involved in the production of nascent HDL particles. ABCA1 transports lipids from peripheral tissues to nascent HDL to form larger HDL particles. Large HDL particles are removed via SR-B1 receptor on the liver into bile, clearance from plasma occurs and Apo1 is recycled. CETP transfers lipids from HDL to non-HDL (LDL-like) particles. Decreasing this transfer is beneficial.

Cell Culture, Treatment, RNA Isolation

Hep-G2 cells were cultured in DMEM (+10% FBS, +5% PenStrep, +5% L-glutamine), while HUVEC cells were cultured in Medium 199 (+25 mg Endothelial Growth Factor, +50 mg Heparin, +20% FBS, +5% PenStrep, +5% L-gluatmine). $3 \times 10^5$ cells were plated in a 6-well plate. Twenty-four hours after plating, the cells were treated (control, Paz 1:100, Paz 1-20, Paz 1-10, New Fraction-4 1:100, New Fraction-4 1:20, New Fraction-4 1-10, Old Fraction-4 1:100, Old Fraction-4 1:20, Old Fraction-4 1:10). Cells were treated for 16 h after which total RNA was isolated using the Qiagen RNeasy Mini Kit and Qiagen QIAshredder, following the protocol provided by the manufacturer.

RNA to cDNA

RNA was converted into cDNA using the High Capacity RNA-CDNA Master Mix (Applied Biosystems), following the protocol provided by the manufacturer starting with 1 μg of total RNA.

RT-PCR

Four primers were obtained from Applied Biosystems: 1) Homo sapiens cholesteryl ester transfer protein (CETP): forward primer sequence ACCTTCTCGCCCACACTGCT (SEQ ID NO: 1), reverse primer sequence TGAAGCCCCA-GGTCTCCAGC (SEQ ID NO: 2); 2) Homo sapiens ATP-Binding cassette, sub family A (ABCA1): forward primer sequence AAGACCCTGGCTTCGGGACC (SEQ ID NO: 3), reverse primer sequence ATG-GTCTGGGGAACTGGGGC (SEQ ID NO: 4); 3) Homo sapiens scavenger receptor class B, member 1 (SR-B1): forward primer sequence AAGAACGTGCGCATCGACCC (SEQ ID NO: 5), reverse primer sequence TCAT-GAAGGCACGTTCGCCG (SEQ ID NO: 6); 4) APOA1: forward primer sequence CATTTCTGGCAGCAAGATGA (SEQ ID NO: 7), reverse primer sequence GCCT-TCAAACTGGGACACAT (SEQ ID NO: 8). Final concentration of primers was 5 μM. Real-time PCRs were carried out in a total of 254 reaction mixture (24 cDNA, 12.54 of 2×SYBR Green PCR Master Mix from Applied Biosystems, 1.0 μL of each 5 μmol/L forward and reverse primers, and 10 μL distilled $H_2O$). The PCR program was initiated by 10 minutes at 95° C. before 50 thermal cycles each at 30 s at 95° C. and 1 min at 60° C. Data were analyzed according to the comparative Ct method and normalized to glyceraldehyde-3-phosphate dehydrogenase expression in each sample (Invitrogen): forward primer sequence ACCCAGAAGACT-GTGGATGG (SEQ ID NO: 9), reverse primer sequence CAGTGAGCTTCCCGTTCAG (SEQ ID NO: 10).

Hamsters

```
1. ABCA1
                                           (SEQ ID NO: 11)
F:  5'-ATAGCAGGCTCCAACCCTGAC-3'

(SEQ ID NO: 12)
R:  5'-GGTACTGAAGCATGTTTCGATGTT-3'

2. CETP
                                           (SEQ ID NO: 13)
F:  F: 5'-AAGGGTGTCGTGGTCAGTTCT--3'

(SEQ ID NO: 14)
R:  F: 5'-ACTGATGATCTCGGGGTTGAT--3'

3. apo A-I
                                           (SEQ ID NO: 15)
F:  5'-ACC-GTTCAG-GAT-GAA-AAC-TGT-AG-3'

(SEQ ID NO: 16)
R:  5'-GTGACT-CAG-GAG-TTC-TGG-GAT-AAC-3'

4. SR-B1
                                           (SEQ ID NO:: 17)
F:  5'-AAG-CCT-GCA-GGT-CTA-TGA-AGC-3'

(SEQ ID NO: 18)
R:  5'-AGA-AAC-CTT-CAT-TGG-GTG-GGT-A-3'
```

Humans

```
    CETP
                                           (SEQ ID NO: 19)
    F:  ACCTTCTCGCCCACACTGCT (SEQ ID NO: 20)
    R:  TGAAGCCCCAGGTCTCCAGC

Sequence (5'->3')
    ABCA1
                                           (SEQ ID NO: 21)
    F:  AAGACCCTGGCTTCGGGACC (SEQ ID NO: 22)
    R:  ATGGTCTGGGGAACTGGGGC Sequence (5'->3')
    SRB1
                                           (SEQ ID NO: 23)
    F:  AAGAACGTGCGCATCGACCC (SEQ ID NO: 24)
    R:  TCATGAAGGCACGTTCGCCG APO-A1
                                           (SEQ ID NO: 25)
    F:  CATTTCTGGCAGCAAGATGA (SEQ ID NO: 26)
    R:  GCCTTCAAACTGGGACACAT
```

Example 4

An alternative approach was employed to explore the mechanism responsible for the more beneficial in plasma lipid profile (lower TC, higher in HDL) achieved by administration of complete PAZ (PP) and fraction 4 of PAZ (PF4) to hamsters fed a high fat diet (preventative model). Quantitative RT-PCR was used to evaluate the relative levels of transcription of specific genes involved in HDL metabolism, i.e. ApoA1, ABCA1, SR-B1, and CETP. In this example, data is shown from five animals/group with three replicates per animal.

Figure 19:
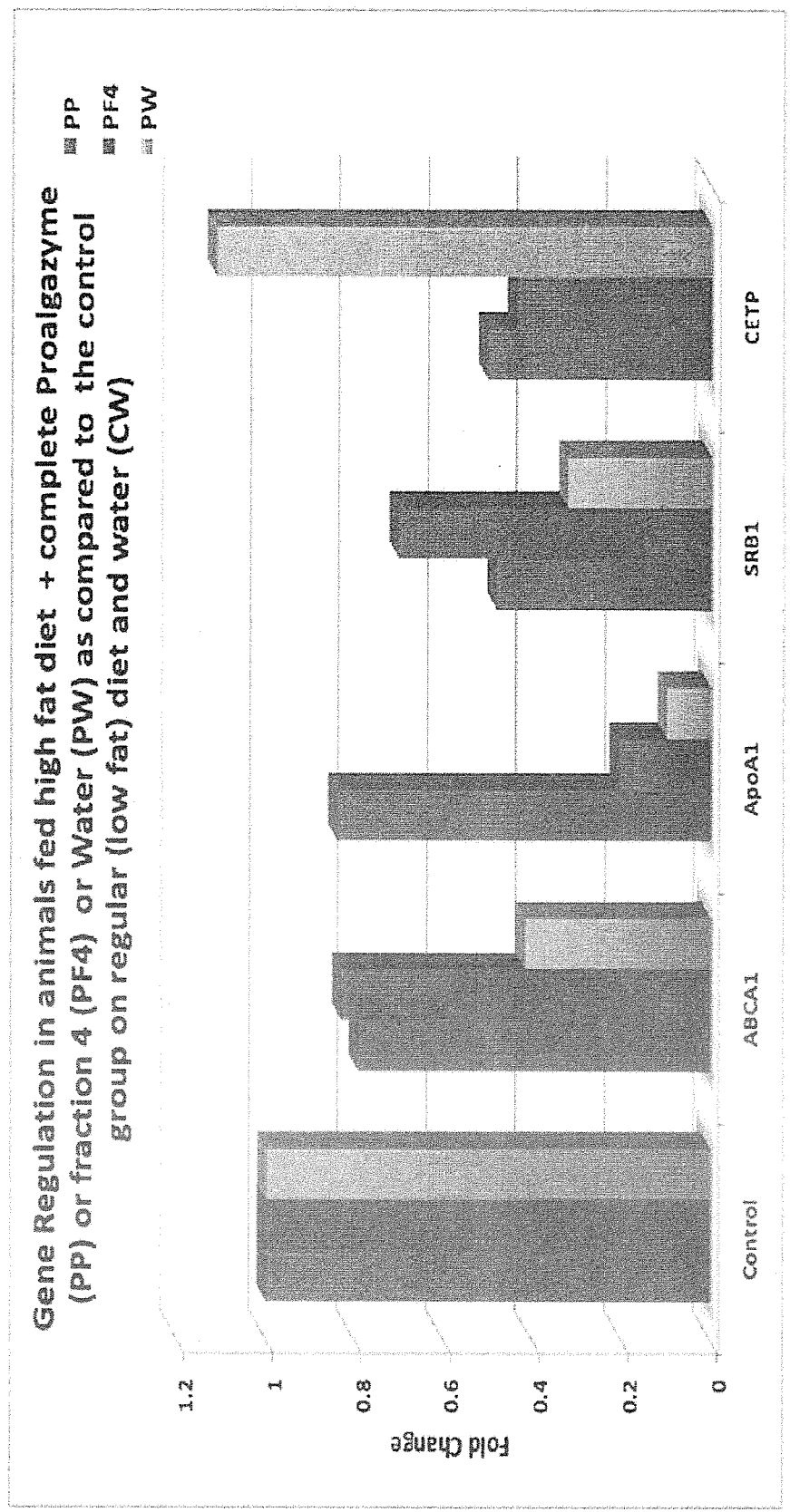
FIG. 19 is a graphical representation of the results obtained in quantitative real time PCR (qPCR) experiments to determine the relative levels of expression of genes that encode key proteins involved in the regulation of cholesterol and HDL metabolism in the liver of hamsters (4 week preventative model) fed either a high fat diet plus complete PAZ (PP), a high fat diet plus one fraction that was isolated from PAZ by a series of chromatographic steps (identified as PF4), or a high fat diet plus water (PW) as compared to the control group on a regular (low fat) diet and water (CW)

FIG. 19 shows a graph of the relative levels of transcription of the specified genes in animals fed a high fat diet plus complete PAZ (PP) or fraction 4 (PF4) or water (PW) as compared to the control group on a regular (low fat) diet and water (CW). The animals fed a high fat diet and water showed an increase in CETP expression, which explains higher plasma LDLc and TC compared to CW and PP/PF4 groups. They also showed a decrease in expression of ApoA1, which correlates with reduced production of HDLc. They also showed a decrease in SR-B1 expression, which correlates with depressed clearance of cholesterol via the reverse cholesterol transport pathway.

Figure 20:
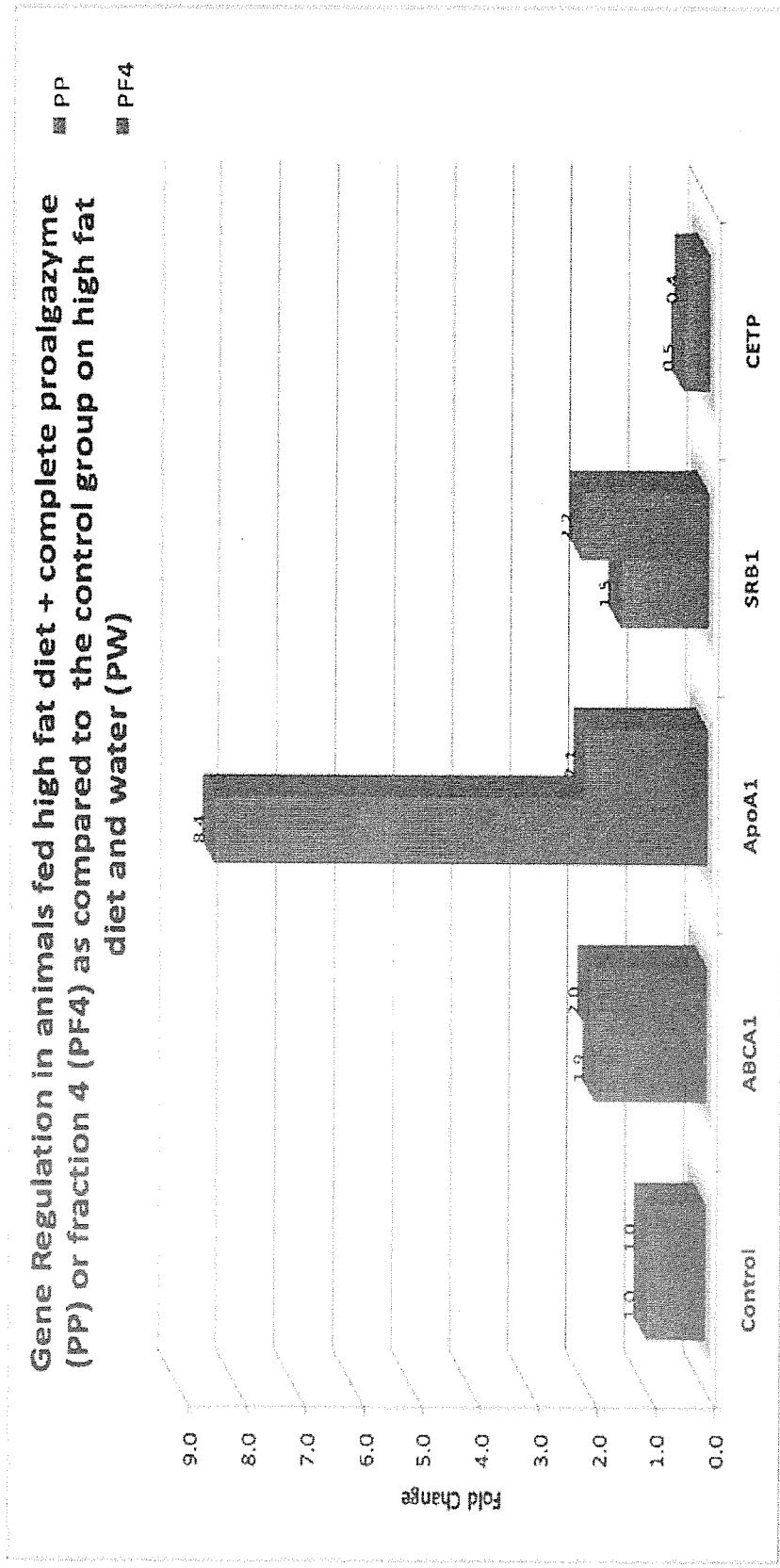
FIG. 20 is a different graphical representation of the results obtained in quantitative real time PCR experiments to determine the relative levels of expression of genes that encode key proteins involved in the regulation of cholesterol and HDL metabolism in the liver of hamsters (4 week preventative model) fed either a high fat diet plus complete PAZ (PP) or fraction PF4 as compared to the control group that was maintained on a high fat diet and water without any additives (PW)

FIG. 20 shows a graph of the relative levels of transcription of the specified genes in animals fed a high fat diet plus complete PAZ (PP) or fraction 4 (PF4) as compared to the control group on high fat diet and water (PW). The ABCA1 and CETP expression levels in PP and PF4 were similar. ApoA1 expression was highly elevated in PP as compared to PF4, which correlates with a much greater production of nascent HDL particles. This can be verified by Western blot and HDL particle size/density. The SR-B1 expression level is higher in the PF4 group, which correlates with an increase in clearance. This correlates with the significant decrease in TC.

In summary, the qPCR analyses of gene regulation using mRNA from hamster liver samples corroborates the changes in lipid plasma profile noted in the study of Example 1, and supports the regulation of the expression of genes encoding key proteins in lipoprotein metabolism as one mechanism of action for PAZ or its components.

Example 5

Fractionation of the active components of PAZ has been significantly hampered by the primary use of long term in vivo methods although, in contrast to high-throughput screening methods typically employed for modern pharmaceutical research which often fail to predict ultimate in vivo effects (both positive and negative), they provide an acid test for in vivo activity. However, given initial results indicating that in vitro assays employing HEPG2 cells to monitor CETP gene expression may provide a surrogate endpoint for screening, the effects of PAZ on CETP expression in cultured HEPG2 cells was further examined.

Figure 21:
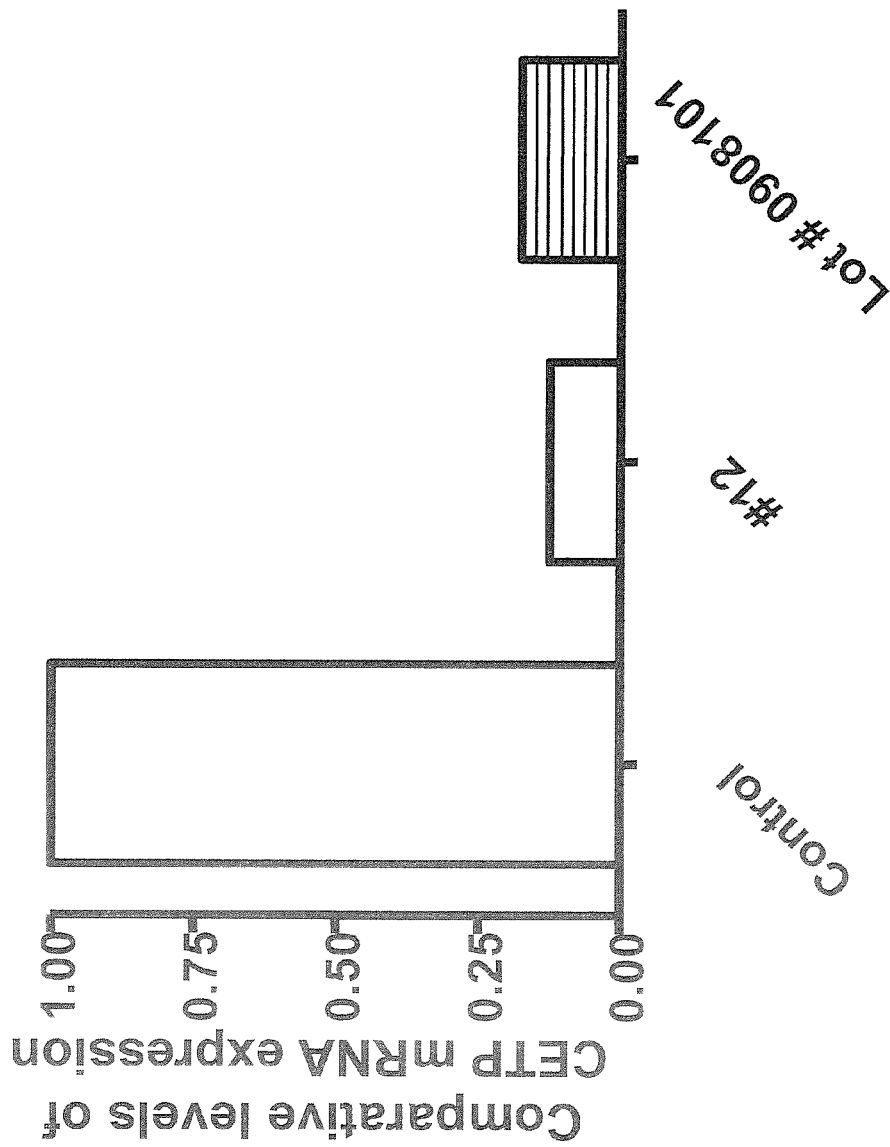
FIG. 21 graphical representation of the results obtained in quantitative real time PCR experiments to determine the relative levels of expression of the gene encoding CETP in the human HEPG2 cell line cultured in medium containing a small aliquot of two different lots of complete PAZ as compared to control cells cultured without any additives.

FIG. 21 illustrates that various production lots of PAZ have potent activity in the reduction of CETP expression in HEPG2 cells.

Figure 22:
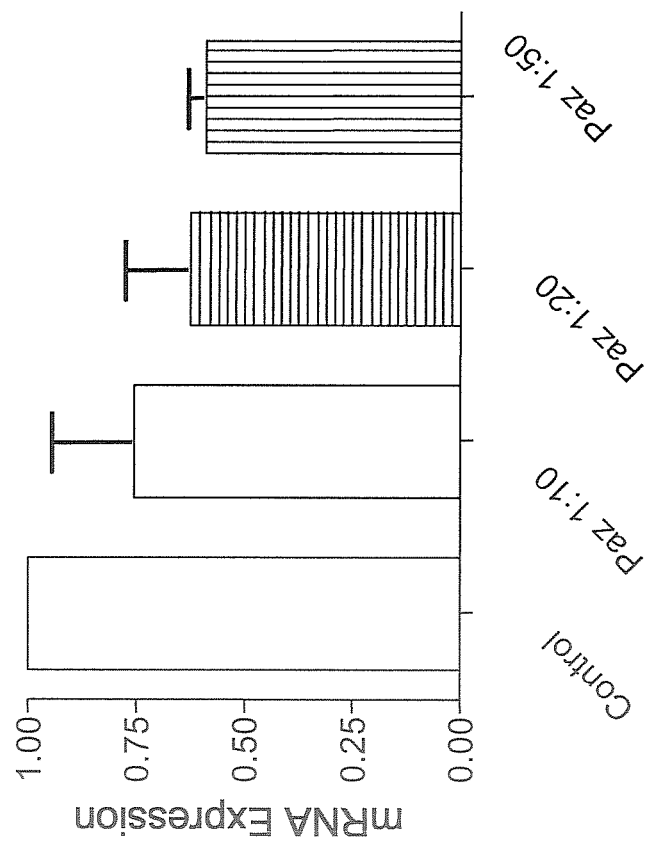
FIG. 22 is a graphical representation of the results obtained in quantitative real time PCR experiments to determine the relative levels of expression of the gene encoding CETP in the human HEPG2 cell line cultured in medium containing various dilutions of complete PAZ as compared to control cells cultured without any additives.

FIG. 22 presents the results of a dose-response study in which increasing dilutions of PAZ in culture medium correlated with increased repression of CETP expression. These data show that (a) PAZ is extremely potent and only low doses are required to achieve a beneficial effect, and/or (b) there can be other components of PAZ that, at certain levels, reduce the beneficial effects of PAZ.

Example 6

Significant beneficial changes in cholesterol and HDL levels, and in the level of expression of certain key genes involved in lipoprotein metabolism that were observed in the in vivo preventative model system. However, given the need for novel agents to treat individuals with hypercholesterolemia, it was important to evaluate the ability of PAZ and fractions derived therefrom to improve the cholesterol and lipoprotein profile in a therapeutic model. The therapeutic hamster experimental model was employed in which the animals (three groups of 8 animals each) were first administered a high fat diet for 28 days, and then co-administered a high fat diet plus PAZ or fractions derived therefrom for an additional 21 days prior to sacrifice. The results obtained are presented in FIGS. 23-25.

Figure 23:
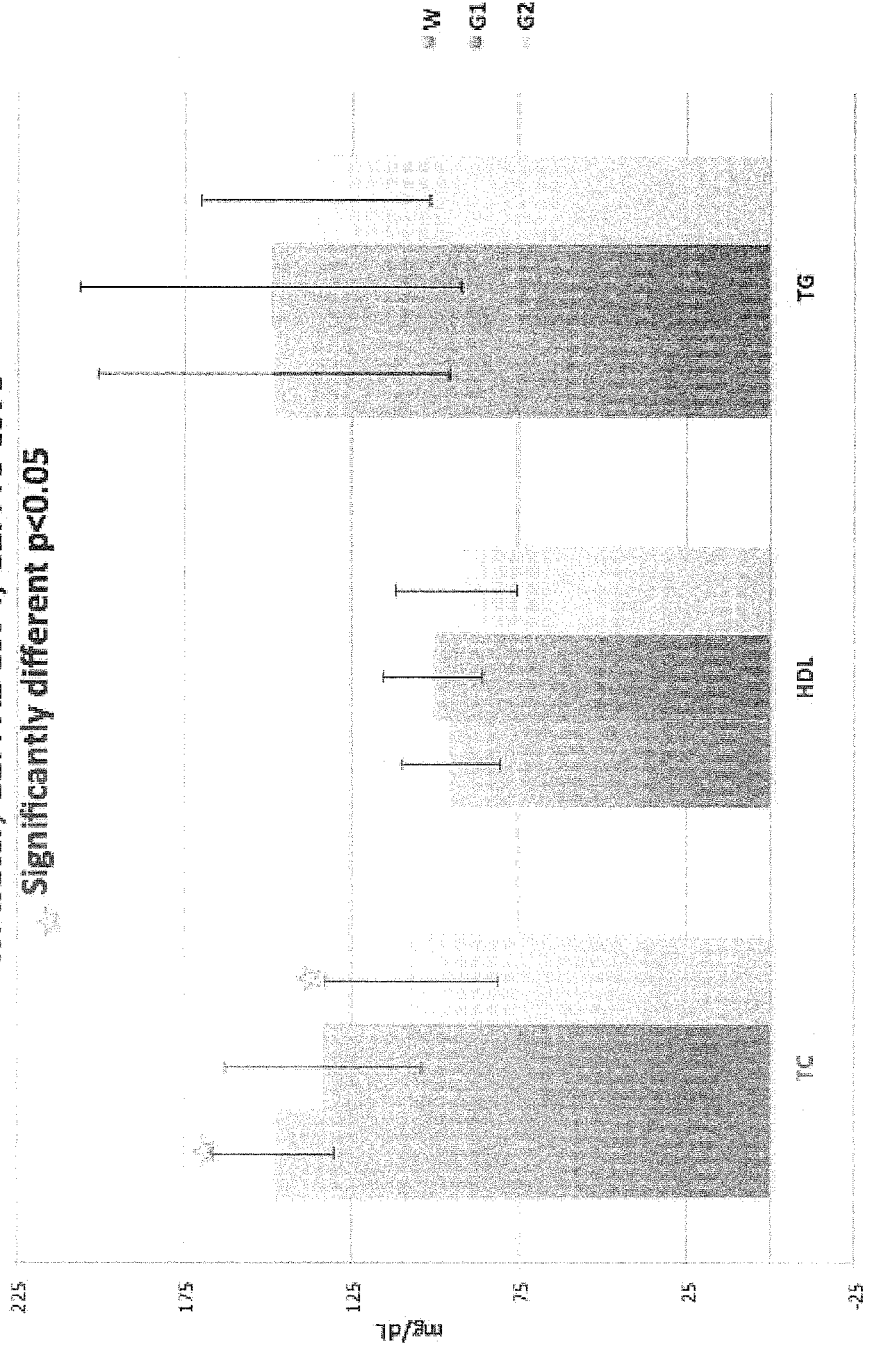
FIG. 23 is a graph of the effect of PAZ and fraction PF3 derived therefrom compared to water without any additives on the total cholesterol levels (mg/dL), the HDL-cholesterol levels (mg/dL) and the triglyceride levels (TG) (mg/dL) of hamsters in an in vivo therapeutic experimental model in which hamsters were first fed a high-fat diet for 4 weeks to induce hypercholesterolemia, and then treated for an additional 21 days with the high fat diet plus complete PAZ (Group 1, G1) or Fraction PF3 (Group 2, G2) derived therefrom.

FIG. 23 presents the effects of PAZ or fraction 3 derived therefrom on the levels of total cholesterol (TC), HDL, and triglycerides in the plasma of hamsters treated with this protocol.

Figure 24:
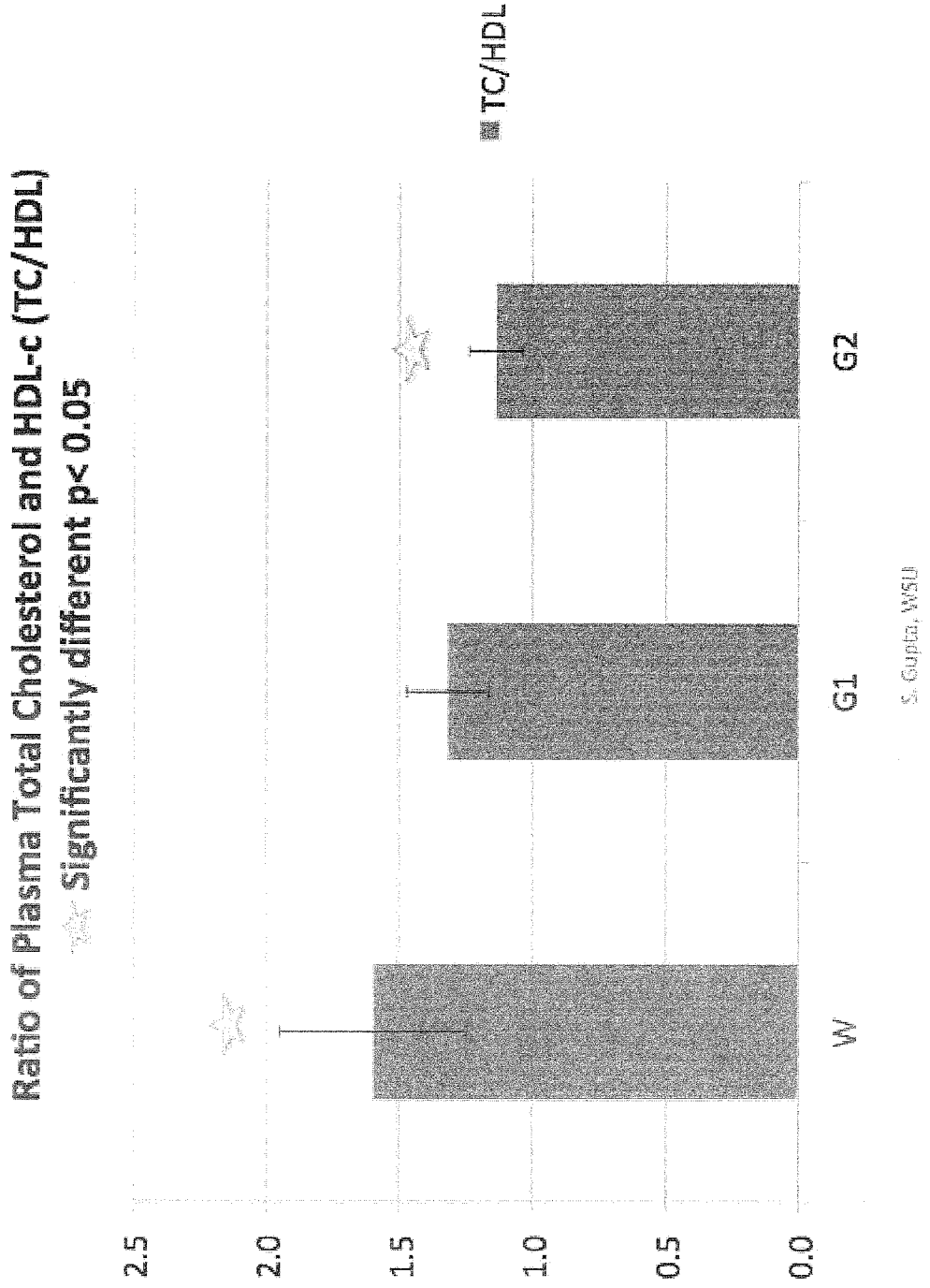
FIG. 24 is a graph of the effect of PAZ and fraction PF3 derived therefrom compared to water without any additives on the ratio of plasma total cholesterol to HDL-cholesterol levels of hamsters in an in vivo therapeutic experimental model in which hamsters were first fed a high-fat diet for 4 weeks to induce hypercholesterolemia, and then treated for an additional 21 days with the high fat diet plus complete PAZ (Group 1, G1) or Fraction PF3 (Group 2, G2) derived therefrom.

FIG. 24 illustrates the reduction in the ratio of cholesterol to HDL affected by therapeutic treatment of hamsters with Fraction 3 of PAZ.

Figure 25:
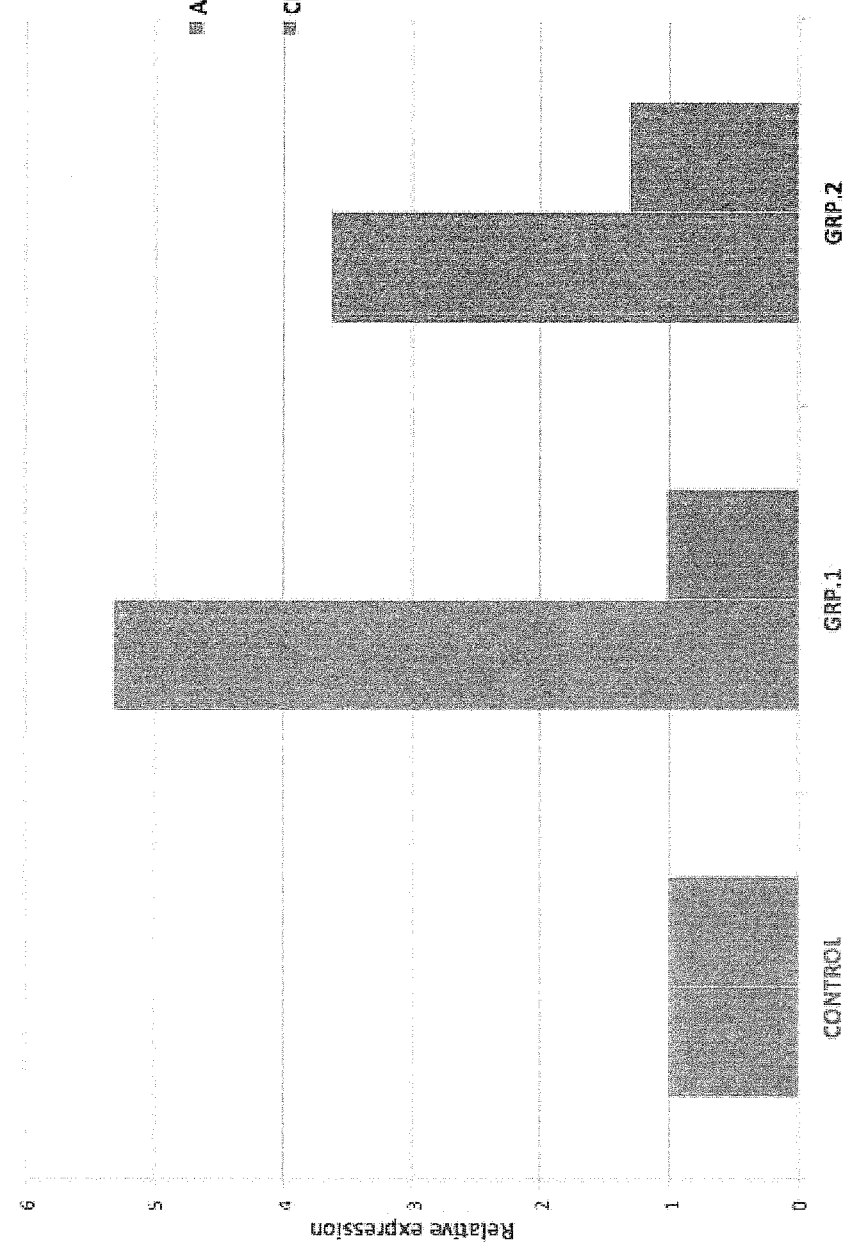
FIG. 25 is a graph of the effect of PAZ and fraction PF3 derived therefrom compared to water without any additives on the expression, using qPCR, of genes encoding the APOA1 and CETP proteins in the liver of hamsters in an in vivo therapeutic experimental model in which hamsters were first fed a high-fat diet for 4 weeks to induce hypercholesterolemia, and then treated for an additional 21 days with the high fat diet plus either complete PAZ (Grp1), Fraction PF3 (Grp2) derived therefrom or water without any additives (W, control)

FIG. 25 illustrates the significant elevation of the expression of the gene encoding ApoA1 in the livers of animals subjected to therapeutic treatment of PAZ for hypercholesterolemia.

Example 7

Given that long term oral administration of PAZ and fractions derived from PAZ are effective in both preventative and therapeutic model systems, that significant beneficial changes in the expression of genes associated with lipoprotein metabolism are observed, and that agents that directly modulate gene expression are likely to cause such changes relatively quickly (although the turnover of lipoproteins and resulting changes in lipoprotein profile may require substantially longer), the ability of PAZ fractions to alter the expression of APOA1 and CETP genes was evaluated in a short term therapeutic model in which animals were pretreated for 28 days with a high fat diet, and then PF3, PF4 (with or without various treatments to concentrate its components) were administered for 7 days (three animals/group) prior to sacrifice and mRNA extraction and qPCR.

Figure 26:
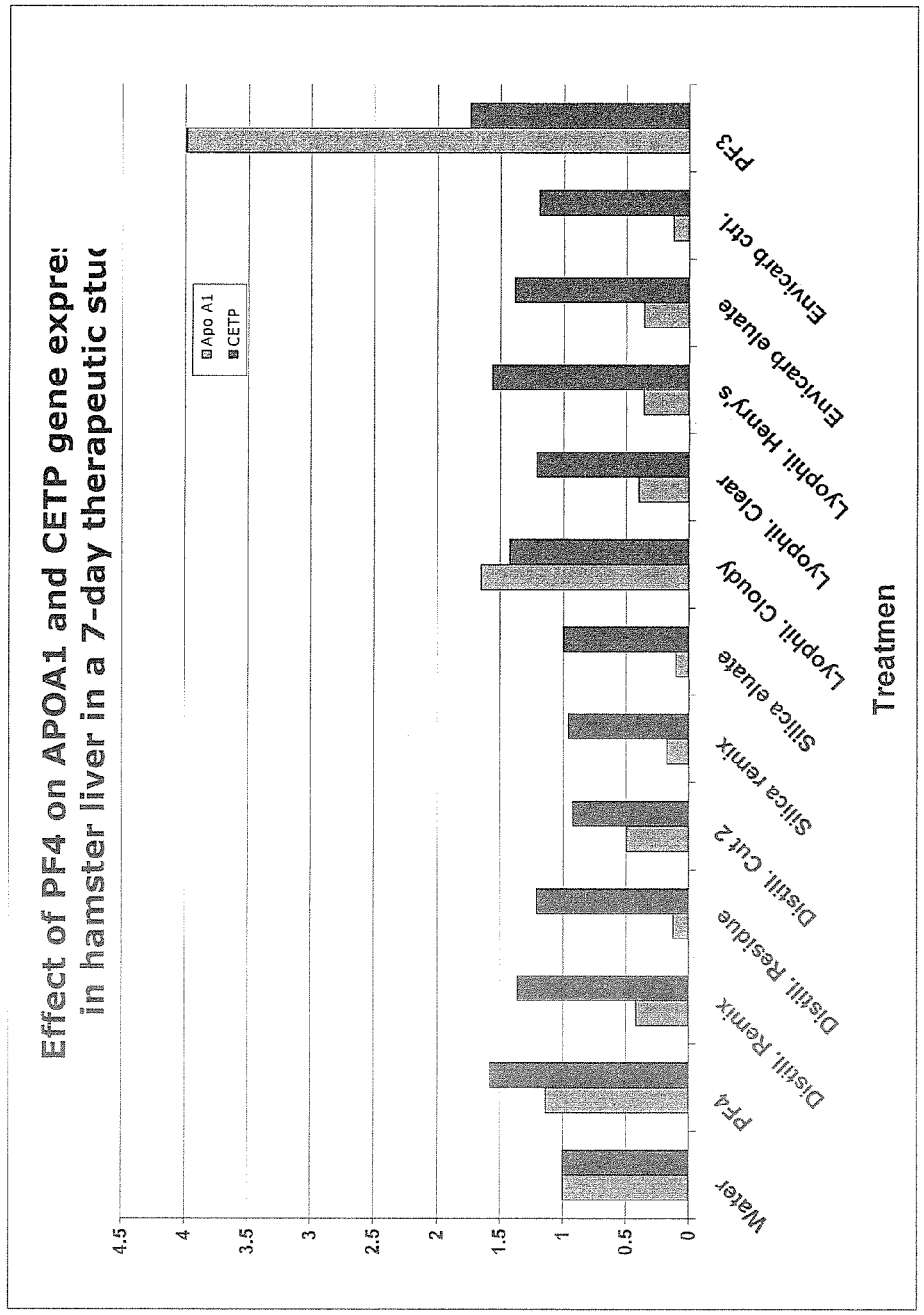
FIG. 26 is a graph of the effect of PAZ fractions PF3, PF4, as well as PF4 following various treatments compared to water without any additives on the expression, using qPCR, of genes encoding the APOA1 and CETP proteins in the liver of hamsters in an in vivo therapeutic experimental model in which hamsters were first fed a high-fat diet for 4 weeks to induce hypercholesterolemia, and then treated for an additional 7 days with the high fat diet plus the specified PF3, PF4 fractions, fraction PF4 following the specified treatments or water without any additives.

FIG. 26 presents the results of these studies. Surprisingly, neither PF4 nor derivatives thereof produced significant enhancement of ApoA1 expression. However, consistent with results obtained in longer therapeutic and preventative studies, fraction PF3 significantly enhanced the expression of ApoA1 in a short-term therapeutic experimental model, suggesting the potential of components in PF3 to directly activate the expression of this gene. Although these data show that the beneficial changes in gene expression observed for PF3, beneficial changes in gene expression were not observed for PF4 in this short-term therapeutic study. However, given the reproducible beneficial changes in gene expression obtained in longer therapeutic and preventative studies, these data support a more complex, possibly indirect mechanism for genetic regulation by PAZ components in fraction PF4.

Example 8

Figure 27:
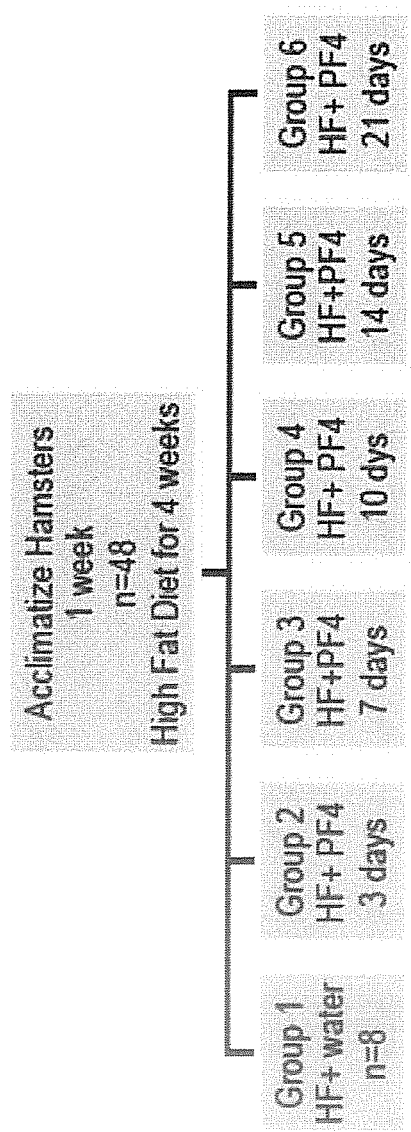
FIG. 27 is a flow chart outlining animal studies performed in an in vivo therapeutic experimental model in hamsters in which a high fat diet was used to produce elevated cholesterol levels and the effect of PAZ fraction PF4 was evaluated for its ability to alter cholesterol metabolism.
Figure 28:
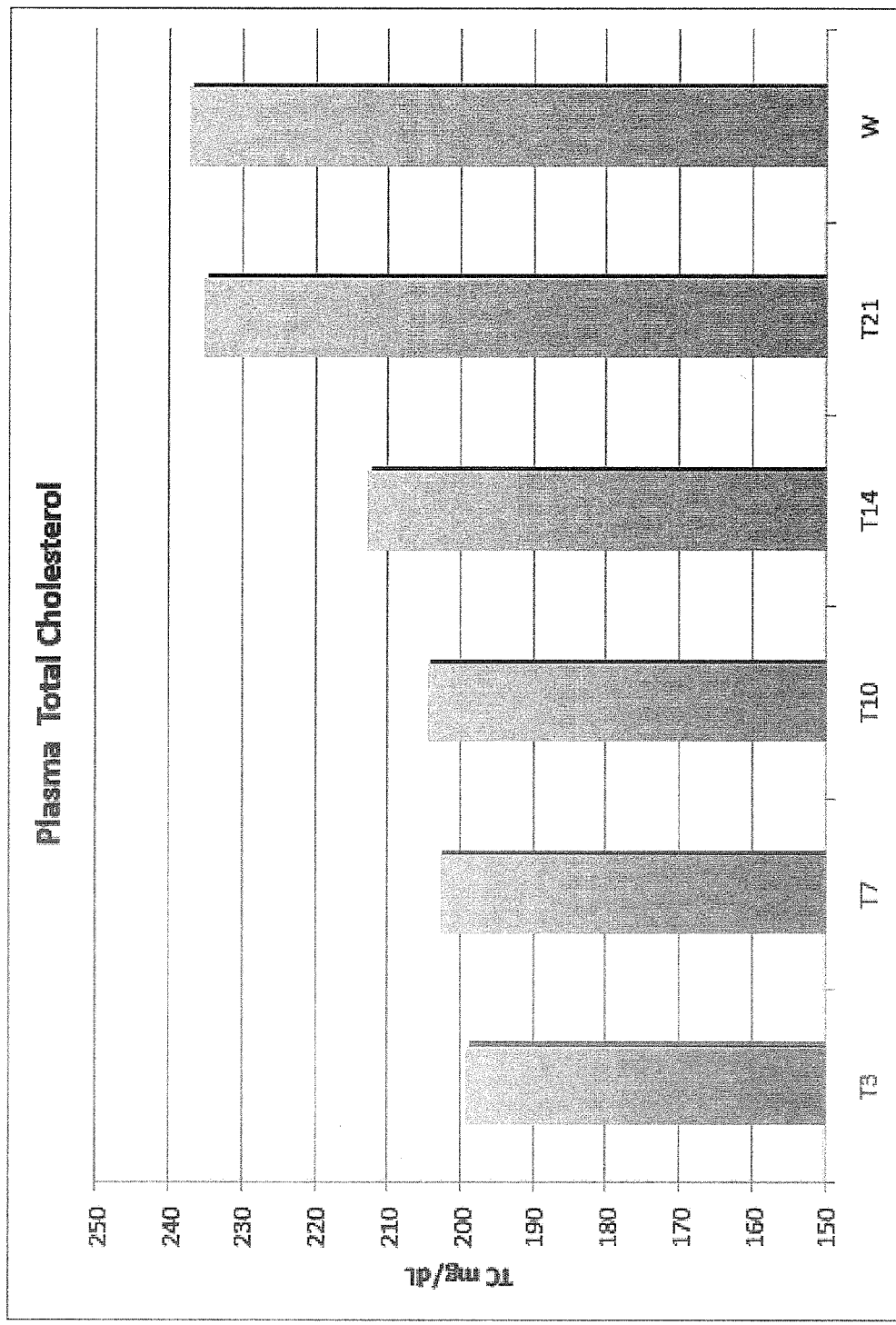
FIG. 28 is a graph of the effects of PAZ fraction PF4 compared to water without any additives on plasma total cholesterol levels (mg/dL) at different time points in hamsters fed a high-fat diet for 4 weeks to induce hypercholesterolemia, and then treated for an additional 21 days with the high fat diet plus either PAZ fraction PF4 or water (control) without any additives.
Figure 29:
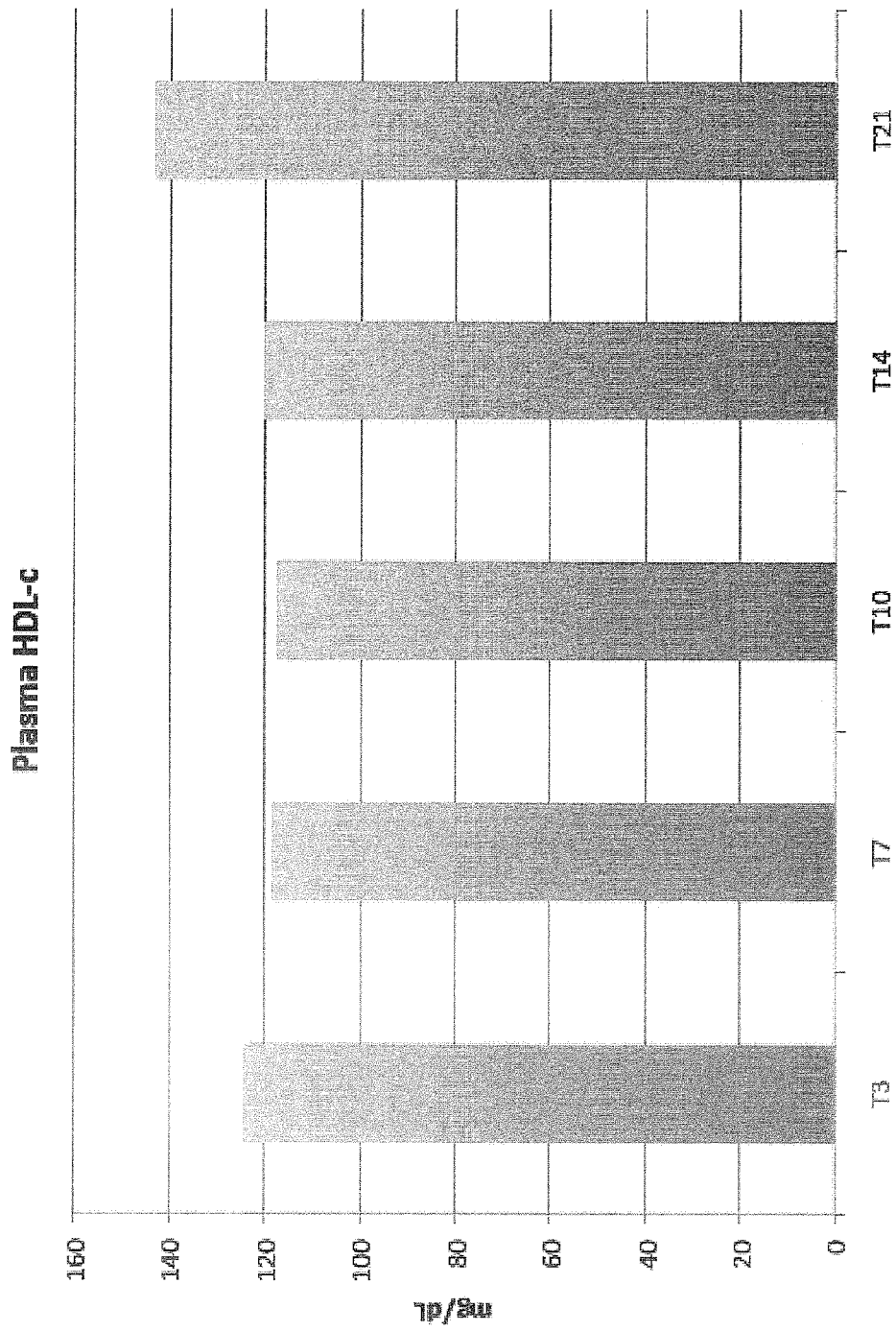
FIG. 29 is a graph of the effects of PAZ fraction PF4 on plasma HDLc levels (mg/dL) at different time points in hamsters fed a high-fat diet for 4 weeks to induce hypercholesterolemia, and then treated for an additional 21 days with the high fat diet plus either PAZ fraction PF4 or water (control) without any additives.
Figure 30:
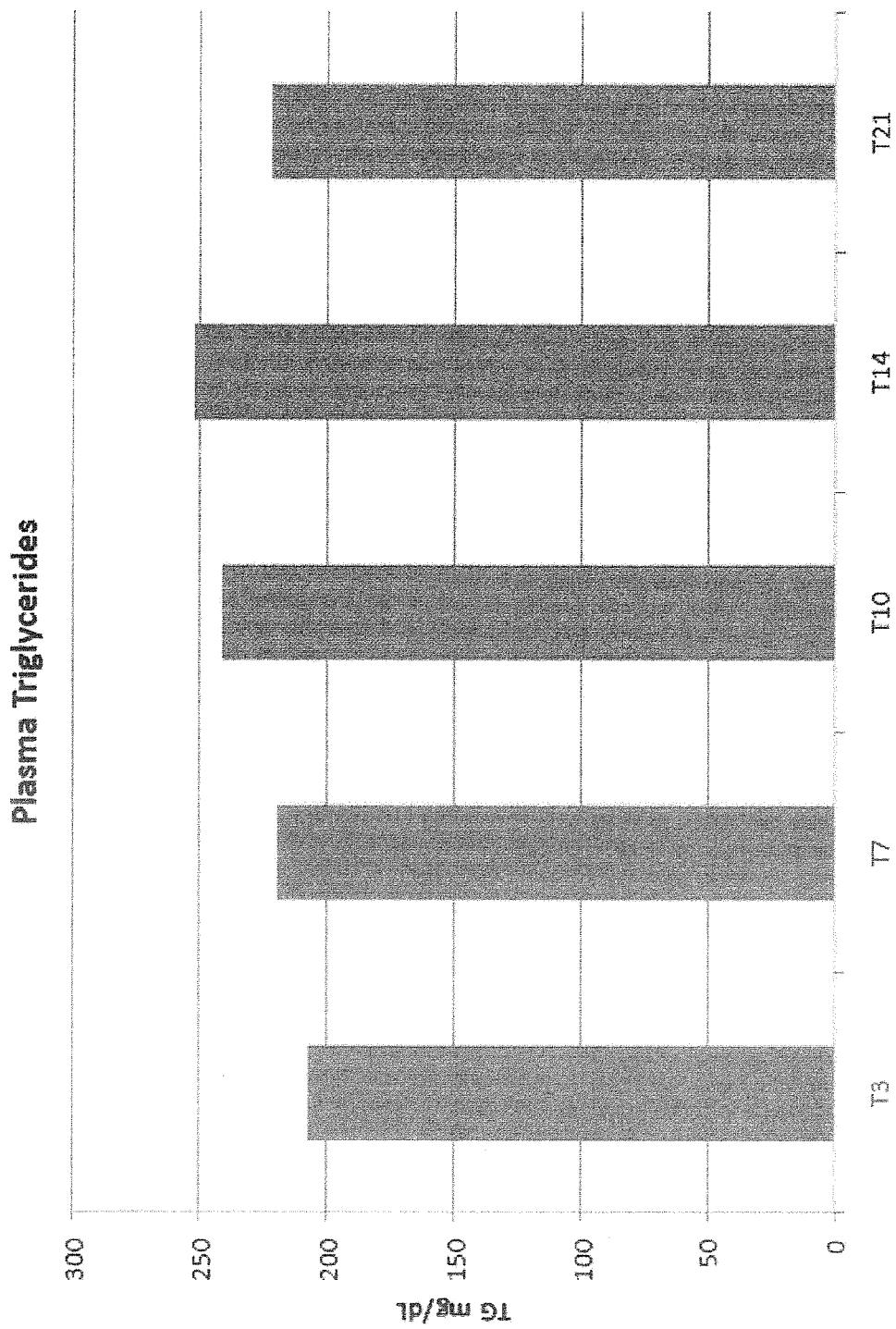
FIG. 30 is a graph of the effects of PAZ fraction PF4 on plasma triglyceride levels (mg/dL) at different time points in hamsters fed a high-fat diet for 4 weeks to induce hypercholesterolemia, and then treated for an additional 21 days with the high fat diet plus either PAZ fraction PF4 or water (control) without any additives.
Figure 31:
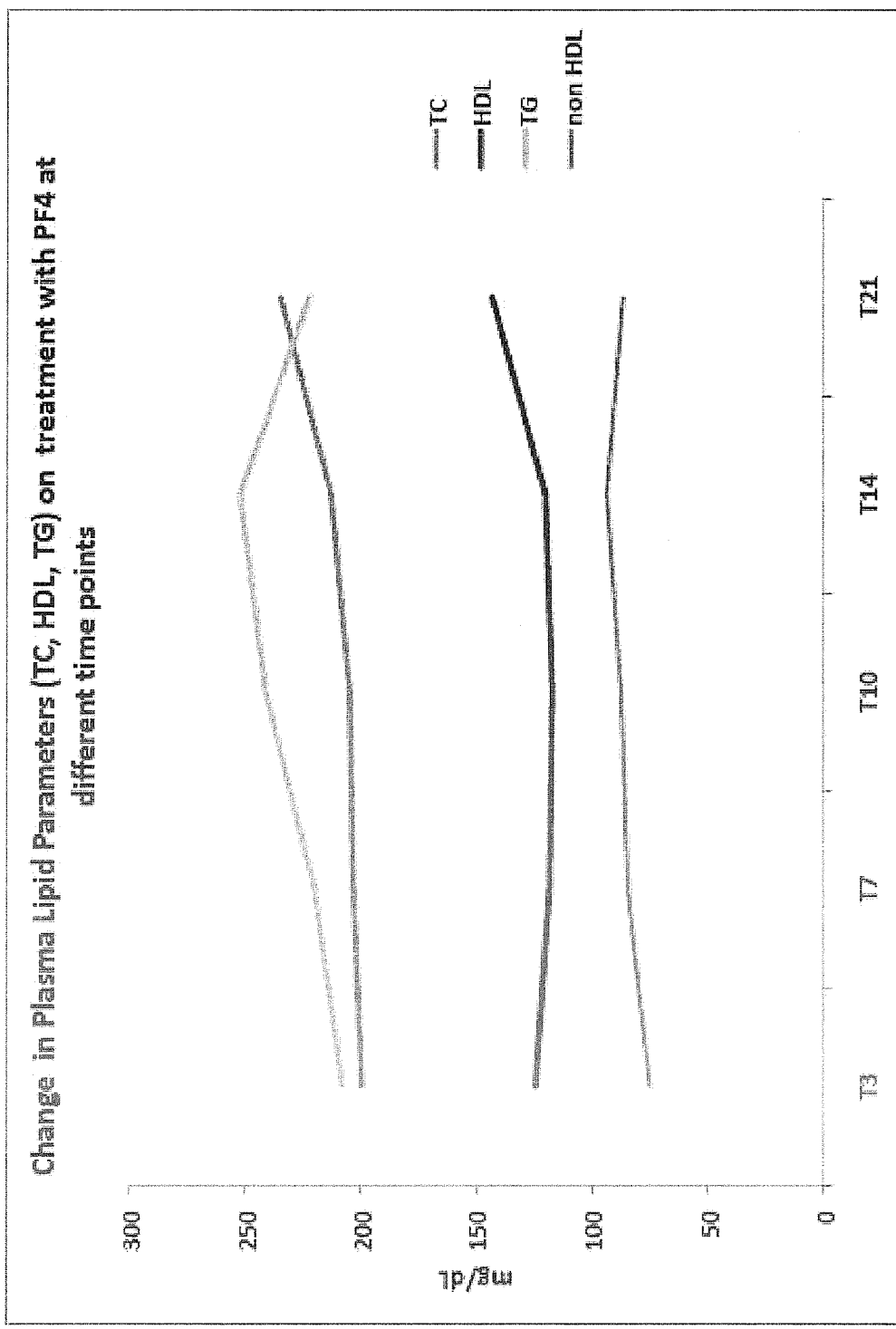
FIG. 31 is a graph comparing the change of various plasma lipid parameters (TC, total cholesterol; HDL; TG, triglycerides; non-HDL) at different time points in hamsters fed a high-fat diet for 4 weeks to induce hypercholesterolemia, and then treated for an additional 21 days with the high fat diet plus either PAZ fraction PF4 or water (control) without any additives.
Figure 32:
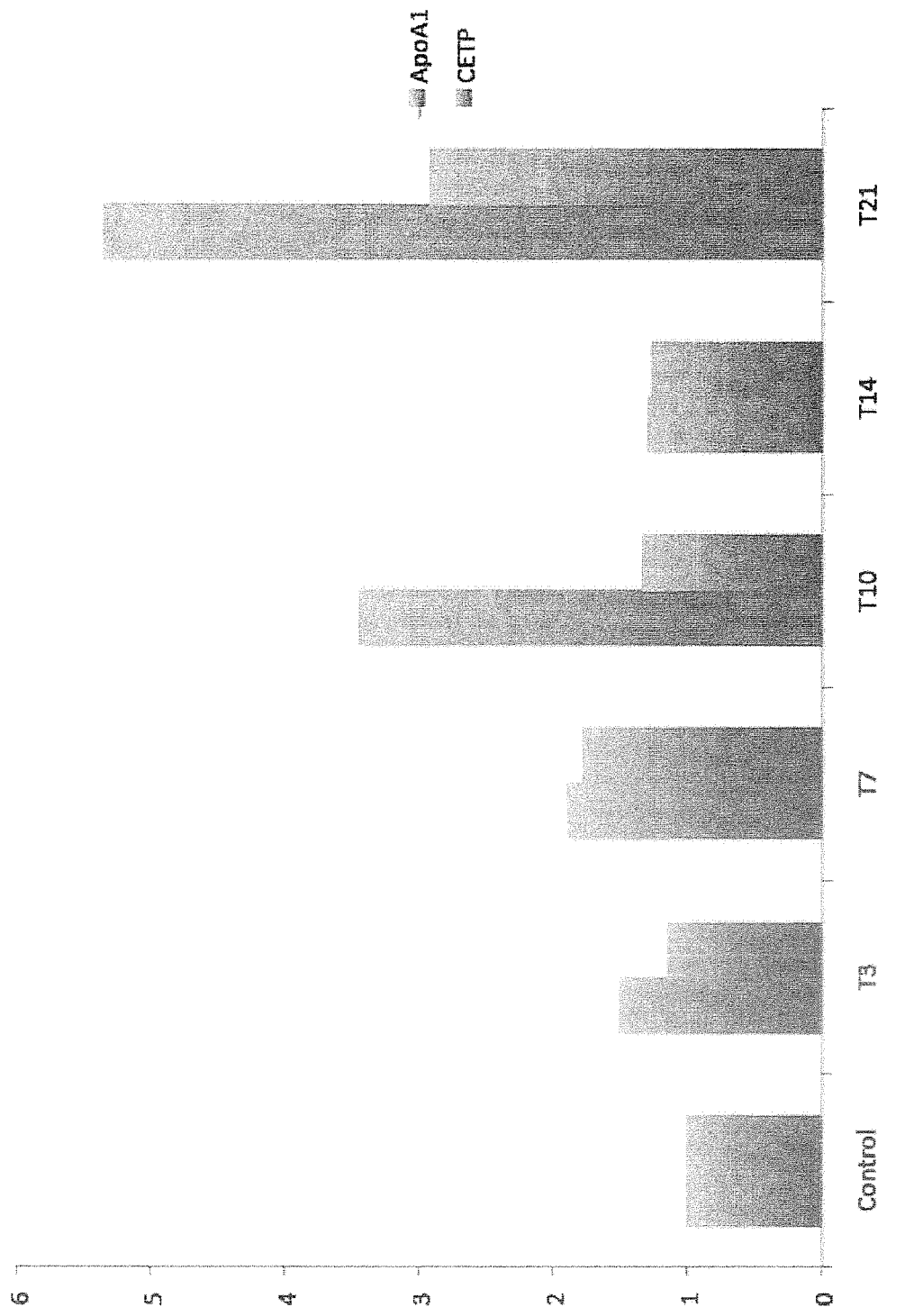
FIG. 32 is a graph of the effect of PAZ fraction PF4 compared to water without any additives on the expression, using qPCR, of genes encoding the APOA1 and CETP proteins in the liver of hamsters in an in vivo therapeutic experimental model in which hamsters were first fed a high-fat diet for 4 weeks to induce hypercholesterolemia, and then treated for an additional 21 days with the high fat diet plus either PAZ fraction PF4 or water (control) without any additives. Groups of hamsters were evaluated at different time points during the 21 day treatment period (3 days, 7 days, 10 days, 14 days and 21 days)

A time study was performed to evaluate the effects of the PF4 Fraction derived from PAZ on cholesterol and lipoprotein metabolism in vivo under therapeutic conditions, i.e. employing an animal model in which hypercholesterolemia was induced prior to administration of PF4. FIG. 27 shows the study design that includes plasma lipid analysis and liver mRNA expression. PF4 is Fraction 4 derived from PAZ using the chromatographic method described in Example 1. The results obtained are presented in FIGS. 27-32. FIG. 28 shows plasma total cholesterol, FIG. 29 shows plasma HDL-c, and FIG. 30 shows plasma triglycerides at different time points. FIG. 31 shows the change in plasma lipid parameters (TC, HDL, TG) on treatment with PF4 at different time points. FIG. 32 shows gene regulation of ApoA1 and CETP at different time points.

FIG. 33 is a comparison of the results obtained in multiple studies of the effects of PAZ fraction PF4 on lipoprotein metabolism parameters in an in vivo experimental model. This time study used the therapeutic approach (4 weeks on HF diet, followed by treatment with PF4). PF4 (lot 3) here at day 21 shows a lipid profile very similar to PF4 (lot 1) after 28 days on a prevention approach (4 weeks of simultaneous HF and PF4 intervention). Both ApoA1 and CETP expression increased at day 21 in the therapeutic time study (PF4/lot 3). ApoA1 increased while CETP decreased using PF4/lot 1 in Example 4 (see FIG. 20). It is possible that the difference in CETP expression that was observed among these studies reflects effects of long-term HF feeding without any agent counteracting its effect in the therapeutic model system.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A method of treating high cholesterol levels in an individual, including the steps of: administering an effective amount of a fraction of a PAZ culture filtrate chosen from the group consisting of PF3 and PF4, wherein if PF3 is administered, further including the step of up-regulating the expression of the gene that encodes ApoA1 and wherein if PF4 is administered, further including the steps of up-regulating the gene that encodes ABCA1 and SR-B1 and down-regulating the expression of the gene that encodes CETP.

2. The method of claim 1, wherein the microbial fermentation product is a liquid oral supplement.

3. The method of claim 1, further including the step of performing an assay to confirm that the up-regulating and down-regulating steps have been performed.

* * * * *

SEQUENCE LISTING

<160> NUMBER OF SEQ ID NOS: 26

<210> SEQ ID NO 1
<211> LENGTH: 20
<212> TYPE: DNA
<213> ORGANISM: Artificial Sequence
<220> FEATURE:
<223> OTHER INFORMATION: Forward PCR primer

<400> SEQUENCE: 1
accttctcgc ccacactgct                                        20

<210> SEQ ID NO 2
<211> LENGTH: 20
<212> TYPE: DNA

```
<213> ORGANISM: Artificial Sequence
<220> FEATURE:
<223> OTHER INFORMATION: Reverse PCR primer

<400> SEQUENCE: 2
tgaagcccca ggtctccagc                                              20

<210> SEQ ID NO 3
<211> LENGTH: 20
<212> TYPE: DNA
<213> ORGANISM: Artificial Sequence
<220> FEATURE:
<223> OTHER INFORMATION: Forward PCR primer

<400> SEQUENCE: 3
aagaccctgg cttcgggacc                                              20

<210> SEQ ID NO 4
<211> LENGTH: 20
<212> TYPE: DNA
<213> ORGANISM: Artificial Sequence
<220> FEATURE:
<223> OTHER INFORMATION: Reverse PCR primer

<400> SEQUENCE: 4
atggtctggg gaactggggc                                              20

<210> SEQ ID NO 5
<211> LENGTH: 20
<212> TYPE: DNA
<213> ORGANISM: Artificial Sequence
<220> FEATURE:
<223> OTHER INFORMATION: Forward PCR primer

<400> SEQUENCE: 5
aagaacgtgc gcatcgaccc                                              20

<210> SEQ ID NO 6
<211> LENGTH: 20
<212> TYPE: DNA
<213> ORGANISM: Artificial Sequence
<220> FEATURE:
<223> OTHER INFORMATION: Reverse PCR primer

<400> SEQUENCE: 6
tcatgaaggc acgttcgccg                                              20

<210> SEQ ID NO 7
<211> LENGTH: 20
<212> TYPE: DNA
<213> ORGANISM: Artificial Sequence
<220> FEATURE:
<223> OTHER INFORMATION: Forward PCR primer

<400> SEQUENCE: 7
catttctggc agcaagatga                                              20

<210> SEQ ID NO 8
<211> LENGTH: 20
<212> TYPE: DNA
<213> ORGANISM: Artificial Sequence
<220> FEATURE:
<223> OTHER INFORMATION: Reverse PCR primer

<400> SEQUENCE: 8
gccttcaaac tgggacacat                                              20
```

```
<210> SEQ ID NO 9
<211> LENGTH: 20
<212> TYPE: DNA
<213> ORGANISM: Artificial Sequence
<220> FEATURE:
<223> OTHER INFORMATION: Forward PCR primer

<400> SEQUENCE: 9
acccagaaga ctgtggatgg                                              20

<210> SEQ ID NO 10
<211> LENGTH: 19
<212> TYPE: DNA
<213> ORGANISM: Artificial Sequence
<220> FEATURE:
<223> OTHER INFORMATION: Reverse PCR primer

<400> SEQUENCE: 10
cagtgagctt cccgttcag                                               19

<210> SEQ ID NO 11
<211> LENGTH: 21
<212> TYPE: DNA
<213> ORGANISM: Artificial Sequence
<220> FEATURE:
<223> OTHER INFORMATION: Forward PCR primer

<400> SEQUENCE: 11
atagcaggct ccaaccctga c                                            21

<210> SEQ ID NO 12
<211> LENGTH: 24
<212> TYPE: DNA
<213> ORGANISM: Artificial Sequence
<220> FEATURE:
<223> OTHER INFORMATION: Reverse PCR primer

<400> SEQUENCE: 12
ggtactgaag catgtttcga tgtt                                         24

<210> SEQ ID NO 13
<211> LENGTH: 21
<212> TYPE: DNA
<213> ORGANISM: Artificial Sequence
<220> FEATURE:
<223> OTHER INFORMATION: Forward PCR primer

<400> SEQUENCE: 13
aagggtgtcg tggtcagttc t                                            21

<210> SEQ ID NO 14
<211> LENGTH: 21
<212> TYPE: DNA
<213> ORGANISM: Artificial Sequence
<220> FEATURE:
<223> OTHER INFORMATION: Reverse PCR primer

<400> SEQUENCE: 14
actgatgatc tcggggttga t                                            21

<210> SEQ ID NO 15
<211> LENGTH: 21
<212> TYPE: DNA
<213> ORGANISM: Artificial Sequence
<220> FEATURE:
```

<223> OTHER INFORMATION: Forward PCR primer

<400> SEQUENCE: 15
accgttcagg atgaaaactg t                                                 21

<210> SEQ ID NO 16
<211> LENGTH: 24
<212> TYPE: DNA
<213> ORGANISM: Artificial Sequence
<220> FEATURE:
<223> OTHER INFORMATION: Reverse PCR primer

<400> SEQUENCE: 16
gtgactcagg agttctggga taac                                              24

<210> SEQ ID NO 17
<211> LENGTH: 21
<212> TYPE: DNA
<213> ORGANISM: Artificial Sequence
<220> FEATURE:
<223> OTHER INFORMATION: Forward PCR primer

<400> SEQUENCE: 17
aagcctgcag gtctatgaag c                                                 21

<210> SEQ ID NO 18
<211> LENGTH: 22
<212> TYPE: DNA
<213> ORGANISM: Artificial Sequence
<220> FEATURE:
<223> OTHER INFORMATION: Reverse PCR primer

<400> SEQUENCE: 18
agaaaccttc attgggtggg ta                                                22

<210> SEQ ID NO 19
<211> LENGTH: 20
<212> TYPE: DNA
<213> ORGANISM: Artificial Sequence
<220> FEATURE:
<223> OTHER INFORMATION: Forward PCR primer

<400> SEQUENCE: 19
accttctcgc ccacactgct                                                   20

<210> SEQ ID NO 20
<211> LENGTH: 20
<212> TYPE: DNA
<213> ORGANISM: Artificial Sequence
<220> FEATURE:
<223> OTHER INFORMATION: Reverse PCR primer

<400> SEQUENCE: 20
tgaagcccca ggtctccagc                                                   20

<210> SEQ ID NO 21
<211> LENGTH: 20
<212> TYPE: DNA
<213> ORGANISM: Artificial Sequence
<220> FEATURE:
<223> OTHER INFORMATION: Forward PCR primer

<400> SEQUENCE: 21
aagaccctgg cttcgggacc                                                   20

```
<210> SEQ ID NO 22
<211> LENGTH: 20
<212> TYPE: DNA
<213> ORGANISM: Artificial Sequence
<220> FEATURE:
<223> OTHER INFORMATION: Reverse PCR primer

<400> SEQUENCE: 22
atggtctggg gaactggggc                                               20

<210> SEQ ID NO 23
<211> LENGTH: 20
<212> TYPE: DNA
<213> ORGANISM: Artificial Sequence
<220> FEATURE:
<223> OTHER INFORMATION: Forward PCR primer

<400> SEQUENCE: 23
aagaacgtgc gcatcgaccc                                               20

<210> SEQ ID NO 24
<211> LENGTH: 20
<212> TYPE: DNA
<213> ORGANISM: Artificial Sequence
<220> FEATURE:
<223> OTHER INFORMATION: Reverse PCR primer

<400> SEQUENCE: 24
tcatgaaggc acgttcgccg                                               20

<210> SEQ ID NO 25
<211> LENGTH: 20
<212> TYPE: DNA
<213> ORGANISM: Artificial Sequence
<220> FEATURE:
<223> OTHER INFORMATION: Forward PCR primer

<400> SEQUENCE: 25
catttctggc agcaagatga                                               20

<210> SEQ ID NO 26
<211> LENGTH: 20
<212> TYPE: DNA
<213> ORGANISM: Artificial Sequence
<220> FEATURE:
<223> OTHER INFORMATION: Reverse PCR primer

<400> SEQUENCE: 26
gccttcaaac tgggacacat                                               20
```